United States Patent [19]
Vornhagen et al.

[11] Patent Number: 6,120,989
[45] Date of Patent: *Sep. 19, 2000

[54] ISOLATED HUMAN CYTOMEGALOVIRUS POLYPEPTIDES AND USES THEREOF

[75] Inventors: Rolf Vornhagen, Langen; Walter Hinderer, Rodgau; Hans-H. Sonneborn, Heusenstamm; Bodo Plachter, Baiersdorf; Gerhard Jahn, Rottenburg, all of Germany

[73] Assignee: Biotest AG, Dreieich, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/506,553

[22] Filed: Jul. 25, 1995

[30] Foreign Application Priority Data

Jul. 26, 1994 [DE] Germany .............................. 44 26 453
Oct. 6, 1994 [DE] Germany .............................. 44 35 789

[51] Int. Cl.$^7$ .............................. C12Q 1/70; C07H 21/04; A61K 39/245
[52] U.S. Cl. .......................... 435/5; 435/69.1; 435/69.3; 435/7.92; 435/7.94; 435/975; 424/185.1; 424/192.1; 424/230.1; 530/324; 530/328; 536/23.72; 930/220
[58] Field of Search .............................. 435/5, 7.92, 69.1, 435/975, 69.3, 7.94; 424/185.1, 192.1, 230.1; 930/220; 536/23.72; 530/324, 328

[56] References Cited

PUBLICATIONS

Ripalti et al. (1994) J. Clin. Microbiol. 32(2): 358–363.
Ripalti et al. (1989) J. Gen. Virol. 70: 1247–1251.
Landini et al. (1991) J. Clin. Microbiol. 29(9): 1868–1872.
Landini et al. (1990) J. Clin. Microbiol. 28(6): 1375–1379.
Smith et al. Gene 67: 31–40, 1988.
Vornhagen et al. (1994) J. Clin. Microbiol. 32(4): 981–986.
Vornhagen et al. (1996) J. Virological Methods 60: 73–80.
Kemble et al. J. Virol. 61(8): 3143–3151, 1987.
Anders et al. J. Virol. 62(4):1364–1372, 1988.
Chee et al. Current Topics in Microbiol. Immunol. 154:125–169, 1990.

*Primary Examiner*—Mary E. Mosher
*Assistant Examiner*—Ali R. Salimi
*Attorney, Agent, or Firm*—Fulbright & Jaworski, LLP

[57] ABSTRACT

Diagnostically relevant polypeptides and fusion proteins comprising an amino acid sequence which originates from cytomegalovirus and corresponds to a region of the major DNA-binding protein or of the C-terminal region of the tegument protein pp150 fused with at least one further fragment from another antigenic protein of cytomegalovirus are disclosed. The major DNA-binding protein is encoded by the reading frame UL57. The poly-peptides and fusion proteins according to the invention can be used in an advantageous manner in diagnostic tests and methods for the detection of IgM antibodies against cytomegalovirus.

27 Claims, 22 Drawing Sheets

PCC15012.SEQ

```
       ----,----+----,----+----,----+----,----+----,----+----,----+
    1  GAATTCTATTCCTCCGTGTTCTTAATC                                      27
```

PCC15013.SEQ

```
       ----,----+----,----+----,----+----,----+----,----+----,----+
    1  CGGATCCTGAAGAGCACGACGGGCAT                                       26
```

PCC525.SEQ

```
       ----,----+----,----+----,----+----,----+----,----+----,----+
    1  GGATCCGCATGCGTGGCAGCCTCTCTTCGCTGGCC                              35
```

PCC526.SEQ

```
       ----,----+----,----+----,----+----,----+----,----+----,----+
    1  GAATTCAGATCTTGCCGCACTTTTGCTTCT                                   30
```

```
GGATCCGCATGCGTGGCAGCCTCTCTTCGCTGGCCAATGCCGGCGGTCTG
----.----+----.----+----.----+----.----+----.----+   50
CCTAGGCGTACGCACCGTCGGAGAGAAGCGACCGGTTACGGCCGCCAGAC
```

IleArgMetArgGlySerLeuSerSerLeuAlaAsnAlaGlyGlyLeu
----.----+----.----+----.----+----.----+----.----+

```
CATGACGACGGCCCGGGTCTGGATAACGATCTCATGAACGAGCCCATGGG
----.----+----.----+----.----+----.----+----.----+  100
GTACTGCTGCCGGGCCCAGACCTATTGCTAGAGTACTTGCTCGGGTACCC
```

HisAspAspGlyProGlyLeuAspAsnAspLeuMetAsnGluProMetGly
----.----+----.----+----.----+----.----+----.----+

```
TCTCGGCGGTCTGGGAGGAGGTGGCGGCGGTGGCGGCAAGAAGCACGACC
----.----+----.----+----.----+----.----+----.----+  150
AGAGCCGCCAGACCCTCCTCCACCGCCGCCACCGCCGTTCTTCGTGCTGG
```

LeuGlyGlyLeuGlyGlyGlyGlyGlyGlyGlyGlyLysLysHisAspArg
----.----+----.----+----.----+----.----+----.----+

```
GCGGTGGCGGCGGTGGTTCCGGTACGCGGAAAATGAGTAGCGGTGGCGGC
----.----+----.----+----.----+----.----+----.----+  200
CGCCACCGCCGCCACCAAGGCCATGCGCCTTTTACTCATCGCCACCGCCG
```

GlyGlyGlyGlyGlySerGlyThrArgLysMetSerSerGlyGlyGly
----.----+----.----+----.----+----.----+----.----+

```
GGCGGTGATCATGACCACGGTCTTTCCTCCAAGGAAAAATACGAGCAGCA
----.----+----.----+----.----+----.----+----.----+  250
CCGCCACTAGTACTGGTGCCAGAAAGGAGGTTCCTTTTATGCTCGTCGT
```

GlyGlyAspHisAspHisGlyLeuSerSerLysGluLysTyrGluGlnHis
----.----+----.----+----.----+----.----+----.----+

FIG. 2A

```
CAAGATCACCAGCTACCTGACGTCCAAAGGTGGATCGGGCGGCGGCGGAG
----.----+----.----+----.----+----.----+----.----+   300
GTTCTAGTGGTCGATGGACTGCAGGTTTCCACCTAGCCCGCCGCCGCCTC

LysIleThrSerTyrLeuThrSerLysGlyGlySerGlyGlyGlyGlyGly
----.----+----.----+----.----+----.----+----.----+

GAGGAGGAGGCGGCGGTTTGGATCGCAACTCCGGCAATTACTTCAACGAC
----.----+----.----+----.----+----.----+----.----+   350
CTCCTCCTCCGCCGCCAAACCTAGCGTTGAGGCCGTTAATGAAGTTGCTG

GlyGlyGlyGlyGlyLeuAspArgAsnSerGlyAsnTyrPheAsnAsp
----.----+----.----+----.----+----.----+----.----+

GCGAAAGAGGAGAGCGACAGCGAGGATTCTGTAACGTTCGAGTTCGTCCC
----.----+----.----+----.----+----.----+----.----+   400
CGCTTTCTCCTCTCGCTGTCGCTCCTAAGACATTGCAAGCTCAAGCAGGG

AlaLysGluGluSerAspSerGluAspSerValThrPheGluPheValPro
----.----+----.----+----.----+----.----+----.----+

TAACACCAAGAAGCAAAAGTGCGGCAAGATCCTGAAGAGCACGACGGGCA
----.----+----.----+----.----+----.----+----.----+   450
ATTGTGGTTCTTCGTTTTCACGCCGTTCTAGGACTTCTCGTGCTGCCCGT

AsnThrLysLysGlnLysCysGlyLysIleLeuLysSerThrThrGlyMet
----.----+----.----+----.----+----.----+----.----+

TGAAAACGGTGGCTTTCGACCTATCGTCGCCCCAGAAGAGCGGTACGGGG
----.----+----.----+----.----+----.----+----.----+   500
ACTTTTGCCACCGAAAGCTGGATAGCAGCGGGGTCTTCTCGCCATGCCCC

LysThrValAlaPheAspLeuSerSerProGlnLysSerGlyThrGly
----.----+----.----+----.----+----.----+----.----+
```

FIG. 2B

```
CCGCAACCGGGTTCTGCCGGCATGGGGGGCGCCAAAACGCCGTCGGACGC
----.----+----.----+----.----+----.----+----.----+   550
GGCGTTGGCCCAAGACGGCCGTACCCCCCGCGGTTTTGCGGCAGCCTGCG

ProGlnProGlySerAlaGlyMetGlyGlyAlaLysThrProSerAspAla
----.----+----.----+----.----+----.----+----.----+

CGTGCAGAACATCCTCCAAAAGATCGAGAAGATTAAGAACACGGAGGAAT
----.----+----.----+----.----+----.----+----.----+   600
GCACGTCTTGTAGGAGGTTTTCTAGCTCTTCTAATTCTTGTGCCTCCTTA

ValGlnAsnIleLeuGlnLysIleGluLysIleLysAsnThrGluGluTer
----.----+----.----+----.----+----.----+----.----+

E
   c
   R
   1

AGAATTC
----.----+   607
TCTTAAG
```

FIG. 2C

| A: CMV-seropositive (n = 54) | Total positive (OD > 0.3) | OD < 0.5 | OD 0.5 < 1.0 | OD > 1.0 |
|---|---|---|---|---|
| 150/7 | 19 | 7 | 8 | 4 |
| 52/3 | 1 | - | 1 | - |
| 52/3\|105/7/2 | 1 | - | 1 | - |

| B: CMV-seropositive (n = 54) | Total positive (OD > 0.3) | OD < 0.5 | OD 0.5 < 1.0 | OD > 1.0 |
|---|---|---|---|---|
| 150/7 | - | - | - | - |
| 52/3 | - | - | - | - |
| 52/3\|150/7/2 | - | - | - | - |

FIG. 5

| Serum | 150/7 | 52/3 | 52/3 I 150 /7/2 |
|---|---|---|---|
| 75332 | 1.576 | 0.353 | 0.736 |
| 81297 | 3.0 | 0.533 | 1.494 |
| 83381 | 3.0 | 0.971 | 2.654 |
| 103850 | 2.473 | 2.305 | 2.189 |
| 112690 | 0.411 | 0.077 | 0.167 |
| 132847 | 1.268 | 0.249 | 0.111 |
| 138076 | 3.0 | 2.019 | 2.518 |
| 145608 | 0.289 | 1.863 | 2.493 |
| 65327 | 1.448 | 0.282 | 1.140 |
| 0162 | 2.742 | 0.203 | 1.434 |
| 1012 | 2.736 | 0.139 | 1.506 |
| 9344 | 2.689 | 0.065 | 2.180 |
| 1744 | 2.427 | 0.030 | 1.704 |
| 1150 | 3.0 | 0.258 | 1.255 |
| 3313 | 3.0 | 0.165 | 0.542 |

FIG. 6

PCCUL571.SEQ

```
    ----,----+----,----+----,----+----,----+----,----+
  1 GGATCCGCATGCATCACGACCGCCTGCTGGACT                    33
```

PCCUL571.SEQ

```
    ----,----+----,----+----,----+----,----+----,----+
  1 GAATTCTTAGTTGTTGATACCCGCATATT                        29
```

PCCUL572

PCCUL577

```
    ----,----+----,----+----,----+----,----+----,----+
  1 GGATCCGCATGCATGGGGTTCCGGGCGGCGGTGC                   34
```

PCCUL577.SEQ

```
    ----,----+----,----+----,----+----,----+----,----+
  1 GAATTCTCTAGAATTGAGCCGATAGGTACGG                      31
```

PCCUL578.SEQ

HC572SY1.SEQ

```
    ----,----+----,----+----,----+----,----+----,----+
  1 GATCCCCTCTAGAGACGCTCAGCGTCTTACTGACGCTGCAGG           42
```

HC572SY1.SEQ

HC572SY2.SEQ

```
    ----,----+----,----+----,----+----,----+----,----+
  1 AATCTCTGCAGCGTCAGTAAGACGCTGAGCGTCTCTAGAGGG           42
```

HC572SY2.SEQ

HC572SY3.SEQ

```
    ----,----+----,----+----,----+----,----+----,----+
  1 GGTGGTGAAGTTCATGACCTTTCTGCTCTTTTCGCTCCGTCTGGTGTTGG   50
 51 TGCAGCTTCTGGTGTTGGTGGG                               72
```

HC572SY3.SEQ

FIG. 7A

```
        ----,----+----,----+----,----+----,----+----,----+
     1  AATCTCCACCAACACCAGAAGCTGCACCAACACCAGACGGAGCGAAAAGA  50
    51  GCAGAAAGGTCATGAACTTCACCACCTGCA                      80

HC572SY4.SEQ
```

HC572SY5.SEQ

```
        ----,----+----,----+----,----+----,----+----,----+
     1  TGGTGGTCTGCTTCTTGGTGAATCTGTTGCTGGTAACTCTATCTGCTTCG  50
    51  GTGTCCCGGGG                                         61

HC572SY5.SEQ
```

HC572SY6.SEQ

```
        ----,----+----,----+----,----+----,----+----,----+
     1  AATTCCCCGGGACACCGAAGCAGATAGAGTTACCAGCAACAGATTCACCA  50
    51  AGAAGCAGACCACCACC                                   67
```

FIG. 7B

```
GGGGTTCCGGGCGGCGGTGCTGGCGGGGGTGGTGGACGAGACGTGAGCGG
----.----+----.----+----.----+----.----+----.----+  50
CCCCAAGGCCCGCCGCCACGACCGCCCCCACCACCTGCTCTGCACTCGCC

GlyValProGlyGlyGlyAlaGlyGlyGlyGlyGlyArgAspValSerGly

----.----+----.----+----.----+----.----+----.----+

GGGCCCGAGCGACGGTCTGGGTGGCGGTCGTGGTGGTGGGGGTGGTGGGG
----.----+----.----+----.----+----.----+----.----+  100
CCCGGGCTCGCTGCCAGACCCACCGCCAGCACCACCACCCCCACCACCCC

GlyProSerAspGlyLeuGlyGlyGlyArgGlyGlyGlyGlyGlyGlyAsp

----.----+----.----+----.----+----.----+----.----+

ATTCCGGGGGAATGATGGGGCGCGGCGGTCGCATGTTGGGCGCTAGCGTG
----.----+----.----+----.----+----.----+----.----+  150
TAAGGCCCCCTTACTACCCCGCGCCGCCAGCGTACAACCCGCGATCGCAC

SerGlyGlyMetMetGlyArgGlyGlyArgMetLeuGlyAlaSerVal

----.----+----.----+----.----+----.----+----.----+

GACCGTACCTATCGGCTCAAT
----.----+----.----+-  171
CTGGCATGGATAGCCGAGTTA

AspArgThrTyrArgLeuAsn

```
                B
                A
                M
                1
ATGGCTAGCATGACTGGTGGACAGCAAATGGGTCGCCGGATCCGCATGCG
----.----+----.----+----.----+----.----+----.----+   50
TACCGATCGTACTGACCACCTGTCGTTTACCCAGCGGCCTAGGCGTACGC

MetAlaSerMetThrGlyGlyGlnGlnMetGlyArgArgIleArgMetArg

----.----+----.----+----.----+----.----+----.----+

TGGCAGCCTCTCTTCGCTGGCCAATGCCGGCGGTCTGCATGACGACGGCC
----.----+----.----+----.----+----.----+----.----+   100
ACCGTCGGAGAGAAGCGACCGGTTACGGCCGCCAGACGTACTGCTGCCGG

GlySerLeuSerSerLeuAlaAsnAlaGlyGlyLeuHisAspAspGlyPro

----.----+----.----+----.----+----.----+----.----+

CGGGTCTGGATAACGATCTCATGAACGAGCCCATGGGTCTCGGCGGTCTG
----.----+----.----+----.----+----.----+----.----+   150
GCCCAGACCTATTGCTAGAGTACTTGCTCGGGTACCCAGAGCCGCCAGAC

GlyLeuAspAsnAspLeuMetAsnGluProMetGlyLeuGlyGlyLeu

----.----+----.----+----.----+----.----+----.----+

GGAGGAGGTGGCGGCGGTGGCGGCAAGAAGCACGACCGCGGTGGCGGCGG
----.----+----.----+----.----+----.----+----.----+   200
CCTCCTCCACCGCCGCCACCGCCGTTCTTCGTGCTGGCGCCACCGCCGCC

GlyGlyGlyGlyGlyGlyGlyGlyLysLysHisAspArgGlyGlyGlyGly

----.----+----.----+----.----+----.----+----.----+

TGGTTCCGGTACGCGGAAAATGAGTAGCGGTGGCGGCGGCGGTGATCATG
----.----+----.----+----.----+----.----+----.----+   250
ACCAAGGCCATGCGCCTTTTACTCATCGCCACCGCCGCCGCCACTAGTAC

GlySerGlyThrArgLysMetSerSerGlyGlyGlyGlyGlyAspHisAsp

```
ACCACGGTCTTTCCTCCAAGGAAAAATACGAGCAGCACAAGATCACCAGC
----.----+----.----+----.----+----.----+----.----+   300
TGGTGCCAGAAAGGAGGTTCCTTTTTATGCTCGTCGTGTTCTAGTGGTCG

HisGlyLeuSerSerLysGluLysTyrGluGlnHisLysIleThrSer

----.----+----.----+----.----+----.----+----.----+

TACCTGACGTCCAAAGGTGGATCGGGCGGCGGCGGAGGAGGAGGAGGCGG
----.----+----.----+----.----+----.----+----.----+   350
ATGGACTGCAGGTTTCCACCTAGCCCGCCGCCGCCTCCTCCTCCTCCGCC

TyrLeuThrSerLysGlyGlySerGlyGlyGlyGlyGlyGlyGlyGly

----.----+----.----+----.----+----.----+----.----+

CGGTTTGGATCGCAACTCCGGCAATTACTTCAACGACGCGAAAGAGGAGA
----.----+----.----+----.----+----.----+----.----+   400
GCCAAACCTAGCGTTGAGGCCGTTAATGAAGTTGCTGCGCTTTCTCCTCT

GlyLeuAspArgAsnSerGlyAsnTyrPheAsnAspAlaLysGluGluSer

----.----+----.----+----.----+----.----+----.----+

GCGACAGCGAGGATTCTGTAACGTTCGAGTTCGTCCCTAACACCAAGAAG
----.----+----.----+----.----+----.----+----.----+   450
CGCTGTCGCTCCTAAGACATTGCAAGCTCAAGCAGGGATTGTGGTTCTTC

AspSerGluAspSerValThrPheGluPheValProAsnThrLysLys

----.----+----.----+----.----+----.----+----.----+

CAAAAGTGCGGCAAGATCCGCATGCATGGGGTTCCGGGCGGCGGTGCTGG
----.----+----.----+----.----+----.----+----.----+   500
GTTTTCACGCCGTTCTAGGCGTACGTACCCCAAGGCCCGCCGCCACGACC

GlnLysCysGlyLysIleArgMetHisGlyValProGlyGlyGlyAlaGly

```
CGGGGGTGGTGGACGAGACGTGAGCGGGGGCCCGAGCGACGGTCTGGGTG
----.----+----.----+----.----+----.----+----.----+  550
GCCCCCACCACCTGCTCTGCACTCGCCCCGGGCTCGCTGCCAGACCCAC

GlyGlyGlyGlyArgAspValSerGlyGlyProSerAspGlyLeuGlyGly

----.----+----.----+----.----+----.----+----.----+

GCGGTCGTGGTGGTGGGGGTGGTGGGGATTCCGGGGGAATGATGGGGCGC
----.----+----.----+----.----+----.----+----.----+  600
CGCCAGCACCACCACCCCCACCACCCCTAAGGCCCCCTTACTACCCCGCG

GlyArgGlyGlyGlyGlyGlyGlyAspSerGlyGlyMetMetGlyArg

----.----+----.----+----.----+----.----+----.----+

GGCGGTCGCATGTTGGGCGCTAGCGTGGACCGTACCTATCGGCTCAATTA
----.----+----.----+----.----+----.----+----.----+  650
CCGCCAGCGTACAACCCGCGATCGCACCTGGCATGGATAGCCGAGTTAAT

GlyGlyArgMetLeuGlyAlaSerValAspArgThrTyrArgLeuAsnTer

ATGGCTAGCATGACTGGTGGACAGCAAATGGGTCGCCGGATCCGCATGCG
----.----+----.----+----.----+----.----+----.----+   50
TACCGATCGTACTGACCACCTGTCGTTTACCCAGCGGCCTAGGCGTACGC

MetAlaSerMetThrGlyGlyGlnGlnMetGlyArgArgIleArgMetArg

----.----+----.----+----.----+----.----+----.----+

TGGCAGCCTCTCTTCGCTGGCCAATGCCGGCGGTCTGCATGACGACGGCC
----.----+----.----+----.----+----.----+----.----+  100
ACCGTCGGAGAGAAGCGACCGGTTACGGCCGCCAGACGTACTGCTGCCGG

GlySerLeuSerSerLeuAlaAsnAlaGlyGlyLeuHisAspAspGlyPro

----.----+----.----+----.----+----.----+----.----+

CGGGTCTGGATAACGATCTCATGAACGAGCCCATGGGTCTCGGCGGTCTG
----.----+----.----+----.----+----.----+----.----+  150
GCCCAGACCTATTGCTAGAGTACTTGCTCGGGTACCCAGAGCCGCCAGAC

GlyLeuAspAsnAspLeuMetAsnGluProMetGlyLeuGlyGlyLeu

----.----+----.----+----.----+----.----+----.----+

GGAGGAGGTGGCGGCGGTGGCGGCAAGAAGCACGACCGCGGTGGCGGCGG
----.----+----.----+----.----+----.----+----.----+  200
CCTCCTCCACCGCCGCCACCGCCGTTCTTCGTGCTGGCGCCACCGCCGCC

GlyGlyGlyGlyGlyGlyGlyGlyLysLysHisAspArgGlyGlyGlyGly

----.----+----.----+----.----+----.----+----.----+

TGGTTCCGGTACGCGGAAAATGAGTAGCGGTGGCGGCGGCGGTGATCATG
----.----+----.----+----.----+----.----+----.----+  250
ACCAAGGCCATGCGCCTTTTACTCATCGCCACCGCCGCCGCCACTAGTAC

GlySerGlyThrArgLysMetSerSerGlyGlyGlyGlyGlyAspHisAsp

```
ACCACGGTCTTTCCTCCAAGGAAAAATACGAGCAGCACAAGATCACCAGC
----.----+----.----+----.----+----.----+----.----+   300
TGGTGCCAGAAAGGAGGTTCCTTTTTATGCTCGTCGTGTTCTAGTGGTCG

HisGlyLeuSerSerLysGluLysTyrGluGlnHisLysIleThrSer

----.----+----.----+----.----+----.----+----.----+

TACCTGACGTCCAAAGGTGGATCGGGCGGCGGCGGAGGAGGAGGAGGCGG
----.----+----.----+----.----+----.----+----.----+   350
ATGGACTGCAGGTTTCCACCTAGCCCGCCGCCGCCTCCTCCTCCTCCGCC

TyrLeuThrSerLysGlyGlySerGlyGlyGlyGlyGlyGlyGlyGlyGly

----.----+----.----+----.----+----.----+----.----+

CGGTTTGGATCGCAACTCCGGCAATTACTTCAACGACGCGAAAGAGGAGA
----.----+----.----+----.----+----.----+----.----+   400
GCCAAACCTAGCGTTGAGGCCGTTAATGAAGTTGCTGCGCTTTCTCCTCT

GlyLeuAspArgAsnSerGlyAsnTyrPheAsnAspAlaLysGluGluSer

----.----+----.----+----.----+----.----+----.----+

GCGACAGCGAGGATTCTGTAACGTTCGAGTTCGTCCCTAACACCAAGAAG
----.----+----.----+----.----+----.----+----.----+   450
CGCTGTCGCTCCTAAGACATTGCAAGCTCAAGCAGGGATTGTGGTTCTTC

AspSerGluAspSerValThrPheGluPheValProAsnThrLysLys

----.----+----.----+----.----+----.----+----.----+

CAAAAGTGCGGCAAGATCCGCATGCATGGGGTTCCGGGCGGCGGTGCTGG
----.----+----.----+----.----+----.----+----.----+   500
GTTTTCACGCCGTTCTAGGCGTACGTACCCCAAGGCCCGCCGCCACGACC

GlnLysCysGlyLysIleArgMetHisGlyValProGlyGlyGlyAlaGly

```
CGGGGGTGGTGGACGAGACGTGAGCGGGGGCCCGAGCGACGGTCTGGGTG
----.----+----.----+----.----+----.----+----.----+   550
GCCCCCACCACCTGCTCTGCACTCGCCCCGGGCTCGCTGCCAGACCCAC

GlyGlyGlyGlyArgAspValSerGlyGlyProSerAspGlyLeuGlyGly

----.----+----.----+----.----+----.----+----.----+

GCGGTCGTGGTGGTGGGGGTGGTGGGGATTCCGGGGGAATGATGGGGCGC
----.----+----.----+----.----+----.----+----.----+   600
CGCCAGCACCACCACCCCCACCACCCCTAAGGCCCCCTTACTACCCCGCG

GlyArgGlyGlyGlyGlyGlyGlyAspSerGlyGlyMetMetGlyArg

----.----+----.----+----.----+----.----+----.----+

GGCGGTCGCATGTTGGGCGCTAGCGTGGACCGTACCTATCGGCTCAATTC
----.----+----.----+----.----+----.----+----.----+   650
CCGCCAGCGTACAACCCGCGATCGCACCTGGCATGGATAGCCGAGTTAAG

GlyGlyArgMetLeuGlyAlaSerValAspArgThrTyrArgLeuAsnSer

----.----+----.----+----.----+----.----+----.----+

TAGAAAGATCCTGAAGAGCACGACGGGCATGAAAACGGTGGCTTTCGACC
----.----+----.----+----.----+----.----+----.----+   700
ATCTTTCTAGGACTTCTCGTGCTGCCCGTACTTTTGCCACCGAAAGCTGG

ArgLysIleLeuLysSerThrThrGlyMetLysThrValAlaPheAspLeu

----.----+----.----+----.----+----.----+----.----+

TATCGTCGCCCCAGAAGAGCGGTACGGGGCCGCAACCGGGTTCTGCCGGC
----.----+----.----+----.----+----.----+----.----+   750
ATAGCAGCGGGGTCTTCTCGCCATGCCCCGGCGTTGGCCCAAGACGGCCG

SerSerProGlnLysSerGlyThrGlyProGlnProGlySerAlaGly

```
ATGGGGGGCGCCAAAACGCCGTCGGACGCCGTGCAGAACATCCTCCAAAA
----.----+----.----+----.----+----.----+----.----+   800
TACCCCCCGCGGTTTTGCGGCAGCCTGCGGCACGTCTTGTAGGAGGTTTT

MetGlyGlyAlaLysThrProSerAspAlaValGlnAsnIleLeuGlnLys

----.----+----.----+----.----+----.----+----.----+

GATCGAGAAGATTAAGAACACGGAGGAATAG
----.----+----.----+----.----+-   831
CTAGCTCTTCTAATTCTTGTGCCTCCTTATC

IleGluLysIleLysAsnThrGluGluTer

|  | Reference test IgM | Reference antigens | | | GST Fusion | | | Autologous Fusion | | | |
|---|---|---|---|---|---|---|---|---|---|---|---|
| Patient No | | 150/7 | 52/3 | UL57/1 | UL57/2 | UL57/3 | 52/3 57/3 | 52/3 57/3 150/7/2 | | UL57/3P |
| 1 | 5.7 | 1.576 | 0.353 | 0.014 | 0.030 | 3.0 | 1.155 | 0.993 | 0.863 |
| 2 | 6.0 | 2.019 | 2.166 | 0.057 | 0.147 | 3.0 | 3.0 | 3.0 | 3.0 |
| 3 | 1.0 | 3.0 | 0.533 | 0.085 | 0.179 | 0.896 | 0.417 | 1.733 | 0.058 |
| 4 | 7.4 | 3.0 | 0.971 | 0.036 | 0.092 | 0.546 | 1.110 | 3.0 | 0.090 |
| 5 | 7.4 | 2.473 | 2.305 | 0.392 | 0.486 | 3.0 | 2.387 | 2.096 | 0.413 |
| 6 | 5.2 | 0.692 | 0.382 | 0.007 | 0.016 | 1.413 | 0.896 | 0.578 | 0.407 |
| 7 | 5.3 | 0.411 | 0.077 | 0.043 | 0.039 | 3.0 | 1.704 | 0.941 | 0.688 |
| 8 | 3.8 | 0.764 | 0.533 | 0.020 | 0.037 | 0.658 | 0.732 | 0.783 | 0.138 |
| 9 | 4.2 | 1.268 | 0.249 | 0.053 | 0.042 | 3.0 | 0.592 | 0.413 | 0.325 |
| 10 | 5.8 | 1.470 | 1.413 | 0.086 | 0.198 | 3.0 | 2.626 | 2.380 | 2.049 |
| 11a 14.8.92 | 2.0 | 3.0 | 0.545 | 0.016 | 0.077 | 3.0 | 0.897 | 0.831 | 0.714 |
| 11b 1.9.92 | 6.0 | 3.0 | 2.019 | 0.061 | 0.118 | 3.0 | 3.0 | 2.700 | 2.807 |
| 12 | 2.1 | 0.289 | 1.863 | 0.052 | 0.231 | 3.0 | 3.0 | 2.778 | 2.818 |
| 13 | nd. | 2.188 | 1.740 | 0.082 | 0.207 | 1.740 | 2.245 | 2.360 | 1.444 |
| Σ 14 above cut-off: | | 13 | 12 | 1 | 1 | 14 | 14 | 14 | 11 |

FIG. 11

| Patient No | Positive cells/ 50000 Antigenemia | Reference antigens | | GST Fusion | | | | Autologous Fusion | | | |
|---|---|---|---|---|---|---|---|---|---|---|---|
| | | 150/7 | 52/3 | UL57/1 | UL57/2 | UL57/3 | 52/3 | 52/3 57/3 | 52/3 57/3 150/7/2 | UL57/3P |
| 1 | 13 | 1.996 | 0.771 | 0.024 | 0.064 | 3.0 | 1.535 | 1.750 | 1.394 |
| 2 | 113 | 0.220 | 0.191 | 0.103 | 0.031 | 0.273 | 0.171 | 0.188 | 0.030 |
| 3 | 15 | 2.648 | 1.186 | 0.021 | 0.037 | 2.051 | 1.397 | 1.458 | 0.925 |
| 4 | 30 | 1.660 | 0.878 | 0.127 | 0.234 | 1.034 | 0.821 | 0.891 | 0.418 |
| 5 | 0 | 2.761 | 1.936 | 0.040 | 0.149 | 3.0 | 3.0 | 3.0 | 3.0 |
| 6 | 135 | 1.768 | 0.993 | 0.813 | 0.123 | 2.697 | 2.742 | 2.352 | 2.662 |
| 7 | 25 | 2.705 | 2.259 | 0.679 | 0.271 | 3.0 | 3.0 | 2.830 | 3.0 |
| 8 | 7 | 0.987 | 0.806 | 0.038 | 0.071 | 2.773 | 1.879 | 0.951 | 1.088 |
| 9 | 40 | 3.0 | 0.404 | 0.069 | 0.087 | 0.980 | 0.688 | 1.803 | 0.135 |
| Σ 9 above cut-off: | | 8 | 8 | 2 | - | 8 | 8 | 8 | 7 |

FIG. 12

| | 150/7 | 52/3 | UL57/1-GST | UL57/2-GST | UL57/3-GST | 52/3 57/3 | 52/3 57/3 150/7/2 | UL57/3P |
|---|---|---|---|---|---|---|---|---|
| A. CMV-seropositive blood donors n = 54 | 19 | 1 | - | - | 1 | 1 | 2 | 1 |
| B. CMV-seronegative blood donors n = 54 | - | - | - | - | 1 | - | - | - |

FIG. 13

| Antigen | Characterization | Reading frame Amino acid range | Diagnostic importance |
|---|---|---|---|
| UL57/1-GST | GST fusion protein | UL57 aa 755-1000 | - |
| UL57/2-GST | GST fusion protein | UL57 aa 1144-1196 | - |
| UL57/3-GST | GST fusion protein | UL57 aa 545-601 | +++ |
| UL57/3-P | Peptide | UL57 aa 545-601 | ++ |
| 52/3 57/3 | Autologous fusion protein | UL44 aa 297-433 +UL57 aa 545-601 | +++ |
| 52/3 57/3 150/7/2 | Autologous fusion protein | UL44 aa 297-433 +UL57 aa 545-601 +UL32 aa 994-1048 | +++ |

ISOLATED HUMAN CYTOMEGALOVIRUS POLYPEPTIDES AND USES THEREOF

FIELD OF THE INVENTION

This invention relates to polypeptides and fusion proteins based upon amino acid sequences of cytomegalovirus (CMV) proteins. Specifically, peptides based upon reading frame UL57, and the C-terminal region of tegument protein pp150 are involved. The invention also involves diagnostic test kit, and methods for detecting CMV specific antibodies. Oligonucleotides encoding the polypeptides and fusing proteins are also disclosed.

BACKGROUND AND PRIOR ART

Infections of humans with human cytomegalovirus (HCMV) are widespread and as a rule proceed without symptoms during childhood. HCMV-specific IgG antibodies, as markers for an infection which has taken place or is latent, can be detected in 50–90% of adults, depending on the population tested. Congenital infection and acute infections in immunosuppressed patients, such as transplant patients and HIV-infected patients, can lead to a life-threatening disease.

To ensure early and effective antiviral treatment, it is of great interest to establish whether an acute infection is present. Various methods can be used for diagnosis of an acute HCMV infection. In transplant patients in particular, in whom constant, concomitant diagnostics are possible, the 'pp65-specific antigenemia test and the polymerase chain reactions, or PCR have become largely accepted in recent years because of their superior sensitivity. In the routine laboratory, an acute infection is as a rule diagnosed, for example in the context of viral differential diagnosis or during pregnancy screening, by detection of the pathogen in the cell culture and serologically by the detection of specific antibodies, in particular in an enzyme linked immunosorbent assay or ELISA. More or less purified, poorly characterized lysates of HCMV-infected cell cultures are currently exclusively used as specific antigens for the antibody detection. This leads to specificity and sensitivity problems, especially in IgM detection. Numerous publications exist which deal with the diagnostic relevance of various recombinant antigens and chemically synthesized peptides. The results available to date are summarized in M. P. Landini: "Antibody Responses to Human Cytomegalovirus Proteins", Reviews in Medical Virology 2, 63–72 (1992) incorporated by reference.

The object of the present invention is therefore to provide polypeptides and/or fusion proteins which are advantageous for diagnostics, as well as test kits which contain these and methods for the detection of acute infections of HCMV.

In the context of the present application, the term polypeptides is understood as meaning biomolecules which consist of α-amino acids and which contain more than 10 amino acids. In respect of the upper limit of the polypeptides, it is to be noted that these are not complete proteins or virtually complete proteins. If the polypeptides according to the invention are in the form of fusion proteins, it is also entirely possible for them to contain more than 100 amino acids. If they are in the form of fusion proteins, it is entirely possible for the polypeptides according to the invention to have a length of up to about 300 amino acids. It is essential, however, that the polypeptides according to the invention contain only certain regions from the proteins of cytomegalovirus.

For diagnostic tests, two aspects are of particular importance. First, the antigens must be highly specific, i.e. in the diagnostic test it must be clearly recognizable that the pathogen is that sought and not a different pathogen. Second, the diagnostic test must be highly sensitive, i.e. every infection with the pathogen sought must be detectable as reliably as possible even if only relatively few antibodies are present in the sample to be analyzed. As far as possible, no false positive results should occur.

The individual proteins encoded by the human cytomegalovirus are as a rule characterized by the reading frame by which they are coded. Landini (loc. cit.) has reported, for example, the genomic location of the various proteins already known for HCM virus. The reading frame can therefore be used for characterization of the protein.

The reading frame UL57 of the human cytomegalovirus codes for the so-called major DNA-binding protein, which has a molecular weight of about 130 to 133 kD. Anders et al. characterized the protein and the reading frame in J. Virology, 62, pages 1364–1372 (1988). Interestingly, the reading frame UL57 has significant homology to the corresponding reading frames of other herpesviruses, in particular to the viruses HHV-6 and to a lesser extent to EBV (Epstein-Barr virus). On the basis of this homology to the reading frames of other viruses, the major DNA-binding protein encoded by UL57 would not actually appear suitable for diagnostics since there is the risk of cross-reactions.

However, in the context of the present invention it has been found, surprisingly, that regions from the reading frame UL57 can be used in a particularly advantageous manner for diagnostics, since polypeptides and fusion proteins which contain this amino acid sequence allow advantageous results to be obtained in diagnostic tests. In the context of the present invention, three fragments were provided from the reading frame UL57, where it was possible for the two fragments UL57/1 and UL57/3 to be amplified by means of the polymerase chain reaction and the fragment UL57/2 was provided by means of chemical DNA synthesis. These DNA fragments were recloned in an expression vector (pGEX-3) which allows expression of the viral proteins in the form of fusion proteins (with glutathione S-transferase (GST)). The fusion proteins were purified and tested with selected sera in ELISA experiments. In these, it was found, surprisingly, that the antigenic fragment UL57/3 consisting of 57 AA is an outstanding antigen for specific and sensitive detection of IgM antibodies present during acute HCMV infection. In contrast, the other two fragments proved to be not diagnostically relevant. Since UL57/3 can be expressed as a non-fusion protein in E. coli only with difficulty, because of its small size, expression was also carried out as an autologous fusion protein together with other diagnostically relevant HCMV antigen fragments, which likewise ensure specific and sensitive IgM serodiagnostics. In the case of the autologous fusion protein 52/3 57/3, expression was carried out C-terminally with amino acids 297–433 of p52. In the case of autologous fusion protein 52/3 57/3 150/7, the 54 C-terminal amino acids of pp150 were additionally expressed at the C-terminal end of 57/3. UL57/3 was furthermore synthesized chemically as a peptide.

The present invention therefore relates to polypeptides comprising an amino acid sequence originating from cytomegalovirus (HCMV), which originates from the reading frame UL57 of the HCM-virus, this reading frame coding for the major DNA-binding protein, which have a homology of at least 60% to the amino acid sequence (SEQ ID NO: 1):

```
Gly Val Pro Gly Gly Gly Ala Gly Gly Gly Gly Gly Arg Asp Val
Ser Gly Gly Pro Ser Asp Gly Leu Gly Gly Gly Arg Gly Gly Gly

Gly Gly Gly Asp Ser Gly Gly Met Met Gly Arg Gly Gly Arg Met

Leu Gly Ala Ser Val Asp Arg Thr Tyr Arg Leu Asn
```

The polypeptides according to the invention preferably have a homology of at least 80% to the amino acid sequence given above. In a particularly preferred embodiment, the polypeptides according to the invention have the amino acid sequence given above or a part sequence thereof. The polypeptides according to the invention usually have a length of at least 10 amino acids; however, polypeptides with a length of at least 25 amino acids are preferred, and polypeptides with a length of at least 40 amino acids are particularly preferred.

The peptides according to the invention can be synthesized by chemical methods which are known per se (for example solid phase synthesis), or can also be prepared by genetic engineering methods.

EPA 87.111726.3 describes a structural phosphoprotein (pp150) of human cytomegalovirus which has proved to be important for detection of specific antibodies.

IgG antibodies directed against HCMV show that infection with human cytomegalovirus has taken place at some time. On the other hand, by determining the titer of IgM antibodies against HCMV, it can be established whether a fresh infection with HCM-viruses is present or not. The answer to this question is of great importance especially for high risk patients mentioned supra for pregnant women. It is of particular importance with such a test that the detection is highly specific and highly sensitive. If too high a number of positive but non-confirmable results is obtained in the test, the test has only a low conclusiveness. On the other hand, however, the test must also reveal fresh HCMV infections with sufficient certainty, but the number of falsely positive results should be reduced as far as possible.

The DNA sequence of cytomegalovirus is already known. Chee et al. disclose, in their publication in Current Topics in Microbiology and Immunobiology, Vol. 154 (1990), pages 125–169, incorporated by reference the locations of the DNA sequence and an analysis of the coding sequences of cytomegalovirus.

In the context of the present invention, it was found that the C-terminal region of the pp150 tegument protein is a very sensitive antigen for detection of IgM antibodies. In the context of the present invention, this is a region of 40 to 60 amino acids on the C-terminus of the pp150 protein. Since the amino acid sequence of pp150 protein is already known, this is the region of amino acids 988 to 1048. The region of the pp150 tegument protein which comprises amino acids 994 to 1048 is particularly preferred in the context of the present invention, and this region is presently designated as pp150/7/2.

According to the invention, this C-terminal region of the pp150 tegument protein binds to a region of high IgM reactivity which originates from another antigen of the HCM-virus. Other antigens are, for example, the antigens called pp65, pp71, pp28 or gp116/58. The antigen p52, and in particular the C-terminal region of the antigen p52, has proven to be a particularly suitable antigen in the context of the present invention.

In the context of the present invention, a region from the C-terminus of p52 which contains about 100 to 150 amino acids of the p52 antigen is thus preferably employed as the other component of the fusion protein. The region from p52 which comprises amino acids 297 to 433 is especially preferred in the context of the present invention.

In the context of the present invention, it has been found that the tegument protein pp150 showed a very high IgM reactivity with sera from healthy blood donors, whereby the value of this antigen is significantly reduced for detection of acute infections. A proportion of about 35% of positive results in the IgM test in healthy, seropositive blood donors is not realistic and shows that the whole pp150 antigen is unsuitable for detection of the IgM antibodies.

It has furthermore been found that the C-terminal region of the p52 antigen merely shows a positive reaction with a serum. Thus, if only p52 were to be used as an antigen, the sensitivity of the assay would not be adequate. The present invention thus also relates to fusion proteins which are prepared by recombination and contain at least one fragment from the C-terminal region of the tegument protein p150 of cytomegalovirus (HCMV) and at least one further fragment from another antigenic protein originating from human cytomegalovirus.

In a preferred embodiment, the other antigenic protein of the fusion protein originates from the protein called p52, wherein a particularly preferred embodiment uses the p52 C-terminal region. In an especially preferred embodiment, this region extends from about the amino acid in position 283 to amino acid No. 433 of p52.

The amino acid sequence of a particularly preferred fusion protein is shown in FIG. 2. For immunological tests, the amino acids can of course be exchanged for amino acids which have functionally the same action without the action of the fusion protein being changed. The expert is fully aware that amino acid exchanges do not affect the immunological properties of a protein as long as the essential structure of the epitopes is not changed. The invention therefore also relates to those fusion proteins which have a homology of at least 80%, and in a particularly preferred form of at least 90%, to the fusion protein shown in FIG. 2. A homology of 80% means that 80 out of 100 amino acids at corresponding points are identical, while 20% of the amino acids may vary.

The fusion proteins just described, which are used according to the invention, comprise (i) the C-terminal part of pp150 and (ii) a region of high IgM reactivity of another cytomegalovirus antigen. Furthermore, the fusion proteins according to the invention can also contain a short amino acid sequence due to the recombinant preparation of the fusion protein. According to the invention, in a preferred embodiment, however, this amino acid sequence, which originates in particular from the expression vector, contains not more than 25 amino acids.

The fusion proteins which can be prepared in this way have an amino acid sequence of a polypeptide or of a fusion protein according to one of claims 1 to 15. Some of the fusion protein preferably originates from glutathione S-transferase. The fusion proteins according to the invention can contain either a polypeptide from the reading frame UL57 of HCM-virus, or a portion of at least one other antigenic protein of human cytomegalovirus. In a particularly preferred embodiment, the other antigenic protein of human cytomegalovirus is the pp150 tegument protein or the p52 protein. Combinations of part sequences of the above-mentioned proteins are particularly preferred.

The present invention also relates to test kits for the detection of antibodies, in particular IgM antibodies, against cytomegalovirus, which comprise at least one polypeptide according to the invention and/or one fusion protein according to the invention. These are preferably test kits for carrying out an ELISA test.

Several different test methods, such as Western blot, radio-immuno-assay and others, are known in diagnostics. Test kits which are particularly preferred in the context of the present invention are those which are suitable for carrying out the ELISA test (enzyme-linked immunosorbent assay). Coupling to a solid phase takes place in these tests. The antigen, in the present case the fusion protein, is often bound to a solid phase, in particular on microtiter plates, and nonspecific bindings sites are saturated. The sample to be analyzed, usually serum, is then introduced into these microtiter plates, incubated and washed. The antibodies bound to the solid phase are then directed against the antigen to be detected. These antibodies are as a rule detected with anti-human antibodies, to which an indicator component is bound. Horseradish peroxidase, which catalyzes a color reaction with the aid of which the test result can be read off, has proved to be particularly suitable here.

An alternative method for detection of specific IgM antibodies is $\mu$-capture ELISA. In this method, the solid phase of a carrier, for example an ELISA plate, is coated with polyclonal or monoclonal antibodies directed against the $\mu$ chain of the human IgM molecule. On subsequent incubation with human serum, IgM antibodies bind selectively to the solid phase, while antibodies of all other classes of antibodies are removed by washing. The CMV-specific IgM antibodies are determined from the large number of bound IgM molecules by means of an enzyme-labeled CMV antigen which is bound by the IgM molecules directed against this antigen. The antibody-antigen complex formed can be detected by an enzyme-mediated color reaction—as already described above.

The present invention also relates to methods for the detection of antibodies against HCMV, in which the sample to be analyzed is brought together with a fusion protein. The antibody-polypeptide or fusion protein complex can then be detected with a detection component. Antigens which display at least some of the "additional sensitivity" of pp150, but at the same time have a high specificity, are also provided by the polypeptides and fusion proteins according to the invention. Only a low IgM reactivity with sera of healthy blood donors is therefore obtained with the polypeptides and fusion proteins according to the invention. With the aid of the polypeptides and fusion proteins according to the invention, it is thus possible to carry out a test for IgM antibodies which detects with adequate sensitivity whether an acute infection is present, and which at the same time considerably reduces, if not excludes completely, the occurrence of false positive results.

Antigens which have a high sensitivity but at the same time a high specificity are provided by the fusion proteins and peptides according to the invention. Only low IgM reactivity with sera of healthy blood donors is therefore obtained with the peptides and fusion proteins according to the invention. With the aid of the peptides and fusion proteins according to the invention, it is thus possible to carry out a test for IgM antibodies which detects with adequate sensitivity whether an acute infection is present and which at the same time considerably reduces, if not even excludes, the occurrence of results which are not clinically relevant or are even false positives.

The detection component is preferably an anti-human antibody which is coupled to an indicator molecule, in particular horseradish peroxidase.

The disclosure of the present invention also enables the expert to synthesize oligonucleotides which comprise a sequence of oligonucleotides which code for an amino acid sequence which corresponds to at least part of the amino acid sequence given in claim 1. The oligonucleotides are preferably 12–30 bases long. They are usually DNA oligonucleotides which can be used for the polymerase chain reaction or other processes which allow amplification of nucleic acids.

The present invention also relates to oligonucleotides which comprise a nucleotide sequence which codes for at least some of the polypeptide UL57/3 according to the invention. Such oligonucleotides can advantageously be employed as a primer in the polymerase chain reaction. Sensitive detection of cytomegalovirus is possible with the aid of the polymerase chain reaction. With this generally known method, detection is possible, e.g., in cases where only a small number of copies of the genetic information of the virus is present.

The term "homology" is understood as meaning the degree of agreement of two DNA or amino acid sequences. 60% homology means, for example, that 60 out of 100 amino acid positions in the sequences coincide. The homology of proteins is determined by sequence analysis.

Since human cytomegalovirus has already been researched relatively thoroughly, the sequence and the reading frame which comprises the peptide according to the invention can be determined with the aid of the publication by Chee et al., Current Topics in Microbiology and Immunology, 154, Springer Verlag (1990), pages 126–169 incorporated by reference.

Fusion proteins which are preferred according to the invention have on the one hand an amino acid sequence of the polypeptide UL57/3 according to the invention and on the other hand a fragment of another protein, in particular another antigenic protein, of human cytomegalovirus and/or a fragment originating from the expression vector. These further constituents of the fusion proteins particularly preferably originate from the tegument protein pp150 and/or from the protein p52 of cytomegalovirus. In an especially preferred form, these are the fragments which are described in the examples of this application.

In the context of the present invention, it has also been found that those fusion proteins which contain at least a portion of glutathione S-transferase (GST) can be expressed easily in *E. coli*. The vectors with which such fusion proteins can be provided has been described, in particular, by Vornhagen et al., Journal of Clinical Microbiology, 32, pages 981–986 (1994).

In the context of the present invention, the antigens were evaluated with:
   a) nonselected sera of healthy blood donors without signs of acute HCMV infection. The sera were classified into HCM-positive/-negative with an anti-CMV IgG ELISA approved by the Paul Ehrlich Institute (Biotest), (See Table 5, infra).
   b) selected sera of immunocompetent (functioning immune system) individuals with an acute HCMV infection, documented by a positive result in virus isolation and/or by IgG seroconversion (See Table 3, infra).

c) selected sera of transplant patients with an acute HCMV primary infection, (See Table 4, infra). The acute infection was detected with the aid of the pp65-specific antigenemia test.

BRIEF DESCRIPTION OF THE FIGURES

FIG. 1 shows the primer for the polymerase chain reaction used for cloning the autologous fusion protein with the designation 52/3|105/7/2. PCC15012.SEQ=SEQ ID NO: 2; PCC15013.SEQ=SEQ ID NO: 3; PCC525.SEQ=SEQ ID NO: 4 and PCC526.SEQ=SEQ ID NO: 5.

FIG. 2 shows the entire DNA sequence of the construction described in Example 1 and the corresponding amino acid sequence of the fusion protein resulting therefrom. This restriction cleavage sites BamH 1 and EcoR1 used for further cloning are identified. Upper strand=SEQ ID NO: 6; lower strand=SEQ ID NO: 7 and amino acid sequence=SEQ ID NO: 8.

FIG. 4 clearly shows that an ambiguous IgM detection is possible with the fusion protein according to the invention, which is not possible, for example, with the fragment 52/3 alone.

FIG. 5 shows Table 1, in which the IgM reactivity of various recombinant antigens is compared on the one hand with the sera of seronegative healthy blood donors and on the other hand with the sera of seropositive healthy blood donors. The fragment portion originating from the tegument protein pp150 (amino acid 862–1048≙150/7) has a high IgM reactivity which is evidently not correlated with illness. When the fusion protein according to the invention (52/3|150/7/2) was used, the number of IgM-positive sera was reduced considerably.

FIG. 6 shows, in Table 2, the OD values in IgM ELISA with sera of different immunocompetent patients with an acute HCMV infection. Compared with the recombinant antigen p52/3, the fusion protein according to the invention shows a significantly improved sensitivity.

FIG. 7 shows the primers and oligonucleotides for the polymerase chain reaction (PCR) used for cloning the various fragments of the reading frame UL57. PCCUL571.SEQ=SEQ ID NO: 9; PCCUL572 =SEQ ID NO: 10; PCCUL577.SEQ=SEQ ID NO: 11; PCCUL578.SEQ=SEQ ID NO: 12; HC572SY1.SEQ=SEQ ID NO: 13; HC572SY2.SEQ=SEQ ID NO: 14; HC572SY3.SEQ=SEQ ID NO: 15; HC672SY4.SEQ=SEQ ID NO: 16; HC572SY5.SEQ=SEQ ID NO: 17, and; HC572SY6.SEQ=SEQ ID NO: 18.

FIG. 8 shows the DNA sequence and the resulting amino acid sequence of the peptide according to the invention from the reading frame UL57 which has been given the designation UL57/3. Upper strand, SEQ ID NO: 19, lower strand, SEQ ID NO: 20, and amino acid sequence, SEQ ID NO: 1.

FIG. 9 shows the DNA and the resulting amino acid sequence of the autologous fusion protein with the abbreviated designation 52/3 57/3. The other part of the fusion protein originates from the antigenic protein p52 of human cytomegalovirus. The BamH1 cleavage site in position 38 was used for expression cloning and characterizes the transition from the vector to the viral sequence. Upper strand, SEQ ID NO: 21, lower strand, SEQ ID NO: 22, and amino acid sequence, SEQ ID NO: 23.

FIG. 10 shows the DNA and the resulting amino acid sequence of the autologous fusion protein 52/3 57/3 150/7/2. In addition to the sequence of the peptide according to the invention, this fusion protein comprises in each case part of the antigenic protein p52 and of the tegument protein pp150. The BamH1 cleavage site in position 38 was used for expression cloning and characterizes the transition from the vector to the viral sequence. Upper strand, SEQ ID NO: 24; lower strand, SEQ ID NO: 25; and amino acid sequence, SEQ ID NO: 26.

FIG. 11 shows, in Table 3, the IgM reactivity with various sera of immunocompetent individuals with an acute HCMV infection. The patient sera are those of patients who have a functioning immune system and an acute HCMV infection.

FIG. 12 shows, in Table 4, the IgM reactivity with sera of transplant patients with an acute HCMV primary infection. Transplant patients regularly do not have a fully functioning immune system, since immunosuppressants are regularly administered in connection with the transplant.

FIG. 13 shows, in Table 5, the IgM reactivity of the recombinant antigens with the sera of healthy blood donors which have been classified into CMV-seropositive on the one hand and CMV-seronegative on the other hand. The differentiation into seropositivity and seronegativity was made by determination of the IgG antibodies. With the peptides and fusion proteins according to the invention, it is advantageous that practically no falsely positive results were obtained.

FIG. 14 shows, in Table 6, a brief characterization of the antigens according to the invention. The abbreviation GST here means that the other constituent of the fusion protein originates from glutathione S-transferase. The abbreviation P means that it is a chemically synthesized peptide.

SUMMARY OF THE INVENTION

Figure 3:
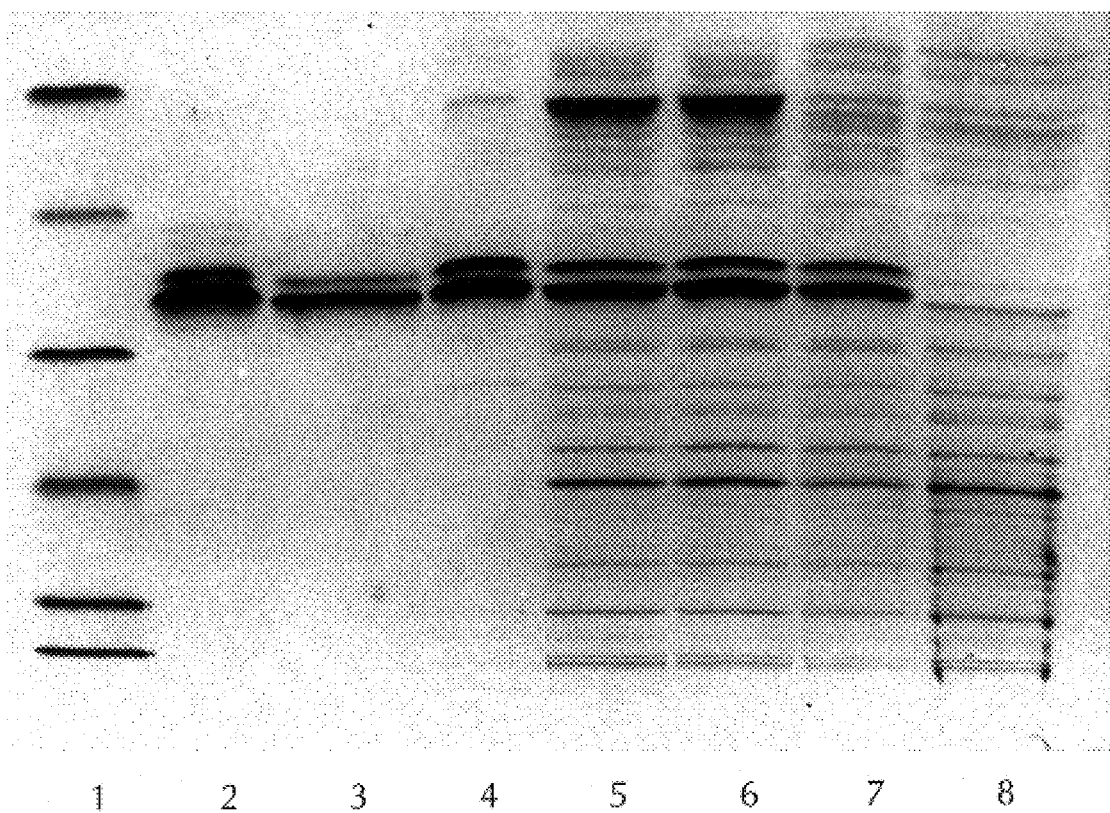
FIG. 3 shows a photograph of an SDS-polyacrylamide gel which demonstrates the expression and purification of the recombinant fusion protein 52/3|150/7/2.

The data clearly show that of the UL57 fragments tested, UL57/3 is particularly relevant diagnostically. This antigenic fragment showed extremely high IgM-specific reactivity with sera of persons with acute HCMV infection. The number of reactive samples was as high as or higher than with the recombinant antigens 150/7 and 52/3 in immunocompetent subjects (Table 3) and also in transplant patients (Table 4). These antigens proved to be particularly suitable for detection of acute HCMV infections in prior evaluation. In contrast, a very low IgM reactivity was found with sera from healthy blood donors. When the autologous fusion proteins were tested, an identical number of positive results were found in both groups of acutely infected patients. Individual differences were to be found only in the level of the reactivity. A somewhat lower IgM-specific prevalence was to be found with the chemically synthesized peptide 57/3-P. Summarizing, it can be stated that the antigen fragment designated UL57/3 is outstandingly suitable for IgM-specific serodiagnostics of acute HCMV infections.

DETAILED DESCRIPTION OF PREFERRED EMBODIMENTS

EXAMPLE 1

Cloning of the Autologous Fusion
Protein 52/3|150/7/2

This is an autologous fusion protein which combines the complete region of 52/3 and the 54 C-terminal amino acids of 150/7.

1. Starting from the clone pUC8/PCC150/7, which comprises the part sequence of pp150 which codes for amino acids ("AA" hereafter) 862–1048, PCR amplification of the part fragment PCC150/7/2 were carried out with the aid of the primers PCC15012.seq and PCC15013.seq (FIG. 1). Both primers have, in addition to the region complementary to pp150, overhangs which comprise certain unique restriction cleavage sites, i.e. PCC15012.seq: EcoRI, PCC15013.seq: BamHI. These cleavage sites allow directed cloning of the amplified product.

The PCR amplification was carried out in a total volume of 100 μl comprising 10 μl of reaction buffer (Perkin-Elmer Cetus), 200 μM of the 4 deoxynucleotides, 0.5 μM of the two PCR primers, 50–100 ng of the starting DNA and 2.5 units of AmpliTaq DNA polymerase (Perkin-Elmer Cetus). The amplification was carried out in a Perkin-Elmer Cetus DNA thermal cycler in 25 cycles under the following conditions: 1 minute—55° C., 1 minute—72° C., 1 minute—94° C. The PCR reaction mixture was fractionated electrophoretically in a submarine agarose gel chamber in a 1.2% agarose gel (Ultra Pure Agarose, BRL) which comprises 0.5 μg/ml ethidium bromide using a TBE running buffer (0.089 M Tris/borate, 0.002 M EDTA). Thereafter, the amplified DNA fragment was visualized with a UV lamp at 364 nm and the gel region which contained the corresponding band was cut out with a scalpel. The DNA was eluted from the gel fragment by means of a Biotrap chamber (Schleicher & Schüll) in accordance with the manufacturer's instructions. This was followed by additional purification of the DNA with an Elutip D column (Schleicher & Schüll) in accordance with the manufacturer's instructions for use.

The DNA fragment thus purified and dried was dissolved in 80 μl of distilled water. After addition of 10 μl of NEBuffer 4 (New England Biolabs), BamHI/EcoRI digestion was carried out by addition of, in each case, 100 U of both enzymes. After 2 hours, phenol extraction followed, with subsequent ethanol precipitation. 100 ng of the DNA fragment thus prepared were ligated with 200 ng of BamHI/EcoRI-treated DNA of the standard vector puc8 for 16 hours at 4° C. and E. coli JM109 was then transformed with this. The transformation mixture was plated out on agar plates to which ampicillin (50 μg/ml) and X-Gal (30 μg/ml) had been added. White colonies were transferred into 3 ml of LB medium with ampicillin and incubated for 12–16 hours at 37° C. while shaking. After the plasmid DNA had been isolated, EcoRI/BamHI restriction digestion and electrophoresis in agarose gel were carried out. A clone in which an additional DNA fragment of the expected size was found was given the name puc8/PCC150/7/2 and was used for further cloning.

2. Starting from the clone puc8/PCC52/3—the cloned fragment codes for AA 297–433 of p52—PCR amplification was carried out with the aid of A primers PCC525.seq and PCC526.seq, and the amplified fragment was later cloned as described above. On the basis of the overhangs of the two primers used here, the amplified fragment has a BamHI cleavage site at the 5'-end and both a BglII and an EcoRI cleavage site at the 3'-end. The corresponding clone was designated puc8/PCC52/3F.

3. Restriction digestion with BamHI and EcoRI was carried out with the DNA of the clone puc8/PCC150/7/2. The fragment of about 160 bp thereby liberated was isolated with the aid of agarose electrophoresis and eluted from the piece of gel cut out, as described above. About 50 ng of this DNA fragment were then ligated with 200 ng of the vector puc8/PCC52/3F opened with BglII and EcoRI and likewise purified by means of electrophoresis. This was followed by transformation with E. coli JM109 and plating out onto ampicillin-containing agar plates. The colonies isolated were transferred into 3 ml of LB medium with ampicillin and incubated for 12–16 hours at 37° C., while shaking. After isolation of the plasmid DNA, BamHI/EcoRI restriction digestion was carried out with subsequent electrophoresis in an agarose gel. A clone with an insert of the expected size was designated puc8/52/3 150/7/2 and used for the further experiments. The fact that the recognition sequences of BamHI and BglII have the same overhangs, which allows ligation, is utilized in this procedure. However, after ligation has been carried out, both cleavage sites are lost. The overhang of 52/3F to 150/7/2 is chosen such that translation in the same reading frame is possible. FIG. 2 shows the entire DNA sequence of the construction described above and the corresponding AA sequence of the resulting autologous fusion protein.

4. To ensure expression of the autologous fusion protein, recloning of the corresponding DNA fragment into the vector pET5c, which has the strong T7 promoter of gene 10 of bacteriophage T7, was carried out. Upstream of this, this vector has a ribosome binding site and a start codon at an appropriate distance. Behind the start codon lies a reading frame of 11 amino acids of gene 10 of bacteriophage T7 and a BamHI and an EcoRI cleavage site. The reading frame of the BamHI cleavage site coincides with that of the autologous fusion protein described above. 100 ng of the DNA fragment liberated from puc8/52/3|150/7/2 by means of EcoRI and BamHI restriction digestion were ligated with 200 ng of the vector cut with the same restriction enzymes for 16 hours at 4° C. Transformation with E. coli JM109 and plating out onto ampicillin-containing plates then followed. The colonies isolated were transferred into 3 ml of LB medium with ampicillin and incubated for 16 hours at 37° C., while shaking. After isolation of the plasmid DNA, BamHI/EcoRI restriction digestion was carried out. A clone with an insert of the size to be expected was designated pET5c/52/3|150/7/2. To ensure expression of the recombinant protein, DNA of the expression vector was transformed into the chloramphenicol-resistant expression strain BL21 (DE3)pLysS. One of the resulting clones was used for further work described herein.

EXAMPLE 2

Expression of Recombinant Fusion Protein 52/3|150/7/2

1. Starting from a plate colony of the clone pET5c/52/3|150/7/2 in BL21(DE3)pLysS, a 15 ml liquid culture—LB medium with ampicillin (Amp) and chloramphenicol (CA)—was cultured at 37° C. in a rotary shaker up to an optical density (600 nm) of 1.8–2.0. Glycerol (87%) was then added to the culture up to a final concentration of 15% (v/v), the mixture was divided into 0.1 ml aliquot portions and these were stored at −60 to −80° C. until used further.

2. A frozen aliquot of the glycerol culture was thawed rapidly and pipetted into 150 ml of LB/CA,AMP medium. This overnight culture was cultured in a liter conical flask (CF) in a rotary shaker at 28° C. and 100 rpm for 16 hours.

3. The 6 l main culture was cultured in 12 parallel batches of 0.5 liter each in 2 liter CF with baffles. The medium (LB/CA,AMP) was preheated to 37° C. After inoculation of the flasks with 10 ml portions of the preculture (1:51), incubation was carried out at 37° C. and 160 rpm in a rotary shaker. The growth was monitored continuously by measurement of the OD at 600 nm. At an OD of 0.6, expression of the recombinant antigen was reduced by addition of IPTG up to a final concentration of 1 mM.

4. Harvesting was carried out 3 hours after induction by centrifugation (6×1 liters beakers, 4000×g, 0–4° C., 30 minutes). The well-drained bacteria pellets were resuspended in 200 ml of ice-cold PBS and centrifuged again (2×250 ml beakers, 5000×g, 0–4° C., 10 minutes). The pellets, well-drained again, were frozen and stored at −20 to −30° C. until processed further.

5. Before the induction and before the harvesting of the bacteria, 1.5 ml aliquots of the bacteria suspension were withdrawn from selected flasks and transferred to an Eppendorf tube and the bacteria were pelleted by centrifugation. The bacteria were then treated with SDS electrophoresis buffer and an aliquot was subjected to analysis by SDS electrophoresis using a 17.5% polyacrylamide gel. The samples taken before harvesting showed an additional, highly pronounced protein double band in the region of 25 k by comparison with the samples taken before the induction.

EXAMPLE 3

Digestion of the Bacteria

The frozen bacteria pellets were thawed, resuspended in 160 ml of base buffer (Tris-HCl/20 mM/pH 7.5) and then homogenized with a Teflon/glass Potter homogenizer. The following additives were then added, while stirring: NP-40 (0.05%), PMSF (0.2 mM), Pefabloc (0.2 mM), EDTA (50 mM) and lysozyme (50 mg) up to a total volume of 200 ml. The mixture was incubated for 60 minutes at room temperature, while stirring vigorously, and was then immediately placed on ice. All the further steps were carried out on ice or with cooling. After the incubation, glycerol (10%) and 2-mercaptoethanol (14 mM) were added and the volume was adjusted to 280 ml with base buffer. The lysis mixture was then subjected to ultrasonic treatment (20 kHz, pulsed, 5 minutes, ¾" titanium probe). Non-solubilized material was removed by centrifugation (2×250 ml beakers, 27000 g, 30 minutes, 0–4° C.). The pellets were discarded.

EXAMPLE 4

Purification of the Recombinant Protein 52/3|150/7/2

1. Solid, finely ground ammonium sulfate was slowly added up to a concentration of 25% saturation to the supernatant from Example 3 while stirring in an ice-bath. Incubation for 15 minutes, while stirring, followed. After centrifugation (2×250 ml beakers, 27000 g, 30 minutes, 0–4° C.), the pellets were discarded. Ammonium sulfate was added again to the supernatant up to a concentration of 45% saturation and the mixture was centrifuged as before. The supernatant was discarded. The pellets were resuspended in 25 ml of base buffer which additionally contained 2-mercaptoethanol (14 mM) and Pefabloc (0.1 mM), frozen and stored overnight at −20 to −30° C.

2. The protein solution fractionated with ammonium sulfate (25–45%) was thawed and precipitated protein was removed by centrifugation (1×50 ml beaker, 40000 g, 30 minutes, 0–4° C.). The supernatant was chromatographed on a Sephadex G-25 (coarse) column (volume at least 200 ml), with absorption being measured at 280 nm. Hereafter, absorption will be abbreviated as "A", followed by the wavelength at which absorption is measured, (280 nm) and the conductivity being measured in the flow-through. Base buffer with 2-mercaptoethanol (1.4 mM) and Pefabloc (0.02 mM) was used as the column buffer. The protein in the exclusion volume was collected in its entirety and immediately chromatographed on SP-Sepharose (Fast Flow). A column of dimensions 2.6×12 cm (60 ml) was used for this. A (280 nm) and the conductivity were recorded continuously. The flow rate was 5 ml/minute and base buffer with 2-mercaptoethanol (1.4 mM) and Pefabloc (0.02 mM) was used as the column buffer. After loading of the sample, followed by 100 ml of column buffer, a linear NaCl gradient (dC/dV=1 mM/ml, up to 300 mM) in the column buffer was applied. The eluate was collected in 10 ml fractions and frozen.

The antigen-containing fractions were in the range between 100 and 200 mM NaCl. Detection was by SDS-PA disk electrophoresis with subsequent Coomassie staining.

3. The fractions which were demonstrated to contain pure antigen (Coomassie gel) were thawed, combined, treated with glycerol (20%) and concentrated by means of ultrafiltration (stirred cell, ice-bath, membrane=Omega 30) to a final concentration of at least 2 mg/ml. The retentate was removed from the chamber, and frozen and stored at −60 to −80° C. in aliquot portions. The course of the purification is documented in FIG. 3.

EXAMPLE 5

Reactivity of the Purified Recombinant Antigen 52/3|150/7/2 in ELISA

1. Test procedure 100 ng portions of the purified recombinant antigen, dissolved in 100 μl of 0.01 M carbonate buffer, pH 9.5, were introduced into the wells of microtiter plates (Nunc) and incubated for 16 hours in an grounded humidity chamber. After addition of 100 μl of a second coating solution containing calf serum, incubation was continued for a further 2 hours. The plates were then emptied and carefully tapped out. The plates were then used for the actual test procedure or, after drying in a vacuum cabinet and subsequent sealing into tubular film, were stored at −20° C. until used later. For the actual test procedure, the test wells of the ELISA plates were filled with 100 μl of serum diluted 1:21, sealed off with a plastic film and incubated for 1 hour at 40° C. floating in a water-bath. After washing three times in a Biotest ELISA Washer II, incubation was carried out with 100 μl of a peroxidase-labeled monoclonal mouse antibody directed against human IgM (Janssen) for 30 minutes at 40° C. After renewed washing, the antibodies bound were visualized by a color reaction with 1,2-phenylenediamine as the chromogen. The optical density of the individual samples was determined at 495 nm (reference: 620 nm) on an Anthos HTII ELISA reader. All OD values greater than 0.3 were evaluated as a positive result.

2. Results

The reactivity was investigated with:

non-selected sera of healthy blood donors without signs of an acute HCMV infection. These sera were classified into HCMV-positive/negative with an approved anti-CMV IgG ELISA (Biotest)

selected sera of immunocompetent individuals with an acute HCMV infection selected courses of kidney transplant patients with an acute HCMV infection.

Table 1 in FIG. 5 shows the IgM reactivity of the autologous fusion protein 52/3|150/7/2 with sera of HCMV-seropositive (n=54) or seronegative healthy blood donors in comparison with the recombinant antigens 52/3 and 150/7, which were likewise expressed in pET5c and purified until homogeneous. While 150/7 showed a high IgM reactivity (<32%) with HCMV-positive sera which evidently did not correlate with the disease, the autologous fusion protein showed the same low reactivity as 52/3 and therefore a significantly better specificity than 150/7.

Table 2 in FIG. 6 shows the OD values in the IgM ELISA described above with 15 sera of immunocompetent persons with an acute HCMV infection. All the sera were positive in the conventional IgM ELISA. Compared with the recombinant antigen 52/3, the autologous fusion protein 52/3|150/7/2 showed a significantly improved sensitivity, i.e. several of the sera negative with 52/3 gave OD values above the cut-off value of 0.3 with the autologous fusion protein.

Figure 4A:
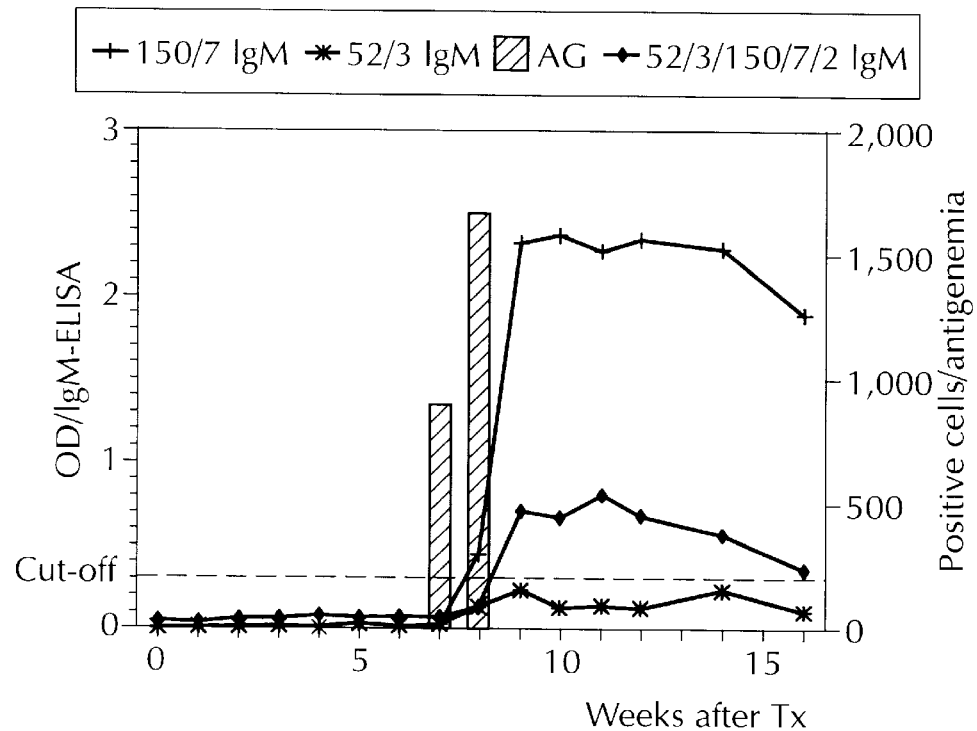
FIG. 4 shows the IgM courses of two patients (top and bottom diagram) in whom in one case a C-terminal fragment of pp150 (amino acid 862–1048) and in one case the C-terminal fragment of p52 (amino acid 297–433) was used in the IgM ELISA. The fusion protein 52/3|150/7/2 according to the invention was also used. The shaded columns designated AG represent the antigenemia values found with other methods. An acute infection was to be observed at these points in time.
Figure 4B:
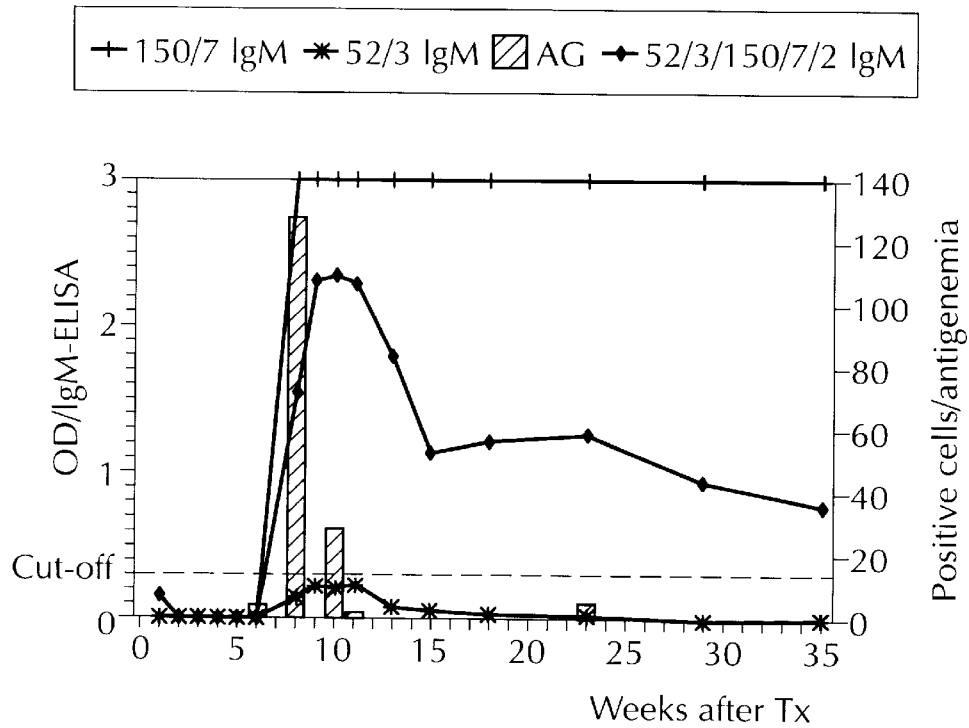

FIG. 4 shows the results of the recombinant proteins 52/3|150/7/2, 52/3 and 150/7 in the IgM ELISA described above with the serum courses of two transplant patients with an acute HCMV primary infection. Both patients were HCMV-seronegative before the transplant and were given an organ (kidney) from a seropositive donor. The course of the acute infection was monitored with the pp65-specific antigenemia test and the PCR. 52/3 showed no IgM reactivity or only a slight IgM reactivity in both courses, while 150/7 showed a strong reactivity. A high IgM-specific seroreactivity, which correlated with the acute course of the disease, resulted in both patients with the autologous fusion protein 52/3|150/7/2.

EXAMPLE 6

PCR Amplification and Cloning of the Fragment UL57/3

Starting from the cosmid clone PCM1029 (Fleckenstein, B., I. Mueller and J. Collins. 1982, Cloning of the complete human cytomegalovirus in cosmids. Gene 18, 39–46), which comprises the entire sequence of UL57, PCR amplification of the part fragment UL57/3, which codes for amino acids 545–601 of the reading frame UL57, took place with the aid of the primers PCCUL577.seq and PCCUL578.seq (FIG. 7). Both primers have, in addition to the region complementary to UL57, overhangs which comprise certain unique restriction cleavage sites, i.e. PCCUL578.seq: EcoRI, PCCUL577.seq: BamHI. These cleavage sites allow directed cloning of the amplified product. The PCR amplification was carried out in a total volume of 100 µl, comprising 10 µl of reaction buffer (Perkin-Elmer Cetus), 200 µM of the 4 deoxynucleotides, 0.5 µM of the two PCR primers, 50–100 ng of the starting DNA and 2.5 units of AmpliTaq DNA polymerase (Perkin-Elmer Cetus). The amplification was carried out in a Perkin-Elmer Cetus DNA thermal cycler in 25 cycles under the following conditions: 1 minute –55° C., 1 minute –72° C., 1 minute 94° C. The PCR reaction mixture was fractionated electrophoretically in a submarine agarose gel chamber in a 1.2% agarose gel (Ultra Pure Agarose, BRL) which comprises 0.5 µg/ml ethidium bromide, using a TBE running buffer (0.089M Tris/borate, 0.002M EDTA). Thereafter the amplified DNA fragment was visualized with a UV lamp at 364 nm and the gel region which contained the corresponding band was cut out with a scalpel. The DNA was eluted from the gel fragment by means of a Biotrap chamber (Schleicher & Schüll), in accordance with the manufacturer's instructions. This was followed by additional purification of the DNA with an Elutip D column (Schleicher & Schüll) in accordance with the manufacturer's instructions for use.

The DNA fragment thus purified and dried was dissolved in 80 µl of distilled water. After addition of 10 µl of NEBuffer 4 (New England Biolabs), BamHI/EcoRI digestion was carried out by addition of in each case 100 U of the two enzymes. After 2 hours, a phenol extraction followed, with subsequent ethanol precipitation. 100 ng of the DNA fragment thus prepared were ligated with 200 ng of BamHI/EcoRI-treated DNA of the standard vector pUC8 for 16 hours at 4° C. and E. coli JM109 was then transformed with this. The transformation mixture was plated out onto agar plates to which ampicillin (50 µg/ml) and X-Gal (30 µg/ml) had been added. White colonies were transferred into 3 ml of LB medium with ampicillin and incubated for 12–16 hours at 37° C., while shaking. After isolation of the plasmid DNA, an EcoRI/BamHI restriction digestion and electrophoresis in agarose gel were carried out. A clone in which an additional DNA fragment of the expected size was found was given the name pUC8/PCCUL57/3 and was used for further cloning.

EXAMPLE 7

PCR Amplification and Cloning of the Part Fragment UL57/1

Starting from the clone PCM1029 (cf. Example 6), PCR amplification of the fragment UL57/1, which codes for amino acids 755–1000 of the reading frame UL57, with the aid of the primers PCCUL571.seq and PCCUL572.seq and later cloning of the amplified fragment were carried out as described above. The corresponding clone was called puc8/PCCUL571.

EXAMPLE 8

Cloning of the Part Fragment UL57/2

PCR Amplification was not possible with this part fragment, in spite of several modifications of the primers. For this reason, the starting DNA to be cloned was synthesized chemically. For this, the amino acid sequence of the fragment was translated into DNA by means of the computer program from DNASTAR, only codons of strongly expressed E. coli genes being used. By slight modification of the DNA sequence, without changing the AA sequence, unique restriction cleavage sites were introduced in order to allow cloning of the chemically synthesized oligonucleotide pairs.

The oligonucleotides were synthesized on a DNA synthesizer 381A from Applied Biosystems, and the subsequent purification of the oligonucleotides was carried out using OPC cartridges (Applied Biosystems) in accordance with the manufacturer's instructions.

10 ng each of the nucleotides HC572SY1.SEQ and HC572SY2.SEQ were ligated with about 200 g of the vector pUC8, opened by means of the restriction enzymes EcoRI and HindIII, for 16 hours at 4° C. and E. coli JM109 was then transformed with these. Plating out on agar plates containing X-Gal/ampicillin and culture of the colonies were carried out as described above. After isolation of the plasmid DNA, restriction digestion was carried out with PstI; this cleavage site was newly introduced by the first oligonucleotide pair. A clone which showed a linearization was used for the further experiments. The DNA of this clone was treated with the restriction enzymes PstI and EcoRI and ligated with 10 ng each of the obligonucleotides HC572SY3.SEQ and HC572.SY4SEQ. Transformation, plating out and isolation were carried out as described above. A clone which had been linearized after restriction digestion with BsgI was used for the third cloning step. After restriction digestion with BsgI and EcoRI, this was carried out with the oligonucleotides HC572SY5.SEQ and HC572SY6.SEQ as described above. A clone which had been linearized with the aid of AvaI was called pUC8/UL57/2 and was used for the further work.

EXAMPLE 9

Cloning of the Fragments UL57/1-3 into the Expression Vector pGEX-3X

To ensure expression of the antigen fragments UL57/1-3 in fusion with the heterologous protein glutathione S-transferase (GST), recloning is carried out in the expression vector pGEX-3X (Smith, D. B., and K. S. Johnson. 1988. Single-step purification of polypeptides expressed in *Escherichia coli* as fusions with glutathione S-transferase. Gene 67, 31–40). This vector has a BamHI cleavage site at the 3' end of the gene which codes for GST. The reading frame of the BamHI cleavage site coincides with those of the coding fragments of the clones pUC8/UL57/1-3. 100 mg of the DNA fragments liberated from pUC8/UL57/1, pUC8/UL57/2 and pUC8/UL57/3 by means of EcoRI and BamHI restriction digestion were ligated with 200 ng of the vector pGEX-3X, opened with the same restriction enzymes, for 16 hours at 4° C. Transformation with *E. coli* JM109 and plating out onto ampicillin-containing plates then followed. The colonies isolated were transferred into 3 ml of LB medium with ampicillin and incubated for 16 hours at 37° C., while shaking. After isolation of the plasmid DNA, a BamHI/EcoRI restriction digestion was carried out. Clones with inserts of the size to be expected were designated pGEX-3/UL57/1, pGEX-3/UL57/2 and pGEX-3/UL57/3 and were used for expression of the UL57 fragments as GST fusion proteins.

EXAMPLE 10

Cloning of the Autologous Fusion Proteins 52/3 57/3 and 52/3 57/3 150/7/2 a) Starting from the clone pUC8/PCC52/3—the cloned fragment codes for AA 297–433 of p52—a PCR amplification with the aid of the primers PCC525.seq and PCC526.seq and later cloning of the amplified fragment were carried out as described above. Because of the overhangs of the two primers used here, the amplified fragment has a BamHI cleavage site on the 5' end and both a BglII and an EcoRI cleavage site on the 3' end. The corresponding clone was designated pUC8/PCC52/3F.

b) Restriction digestion was carried out with DNA of the clone pUC8/UL57/3 using the restriction enzymes XbaI and EcoRI. 200 ng of the vector thus opened were ligated with 10 ng each of the two oligonucleotides UL57F3.SEQ and UL57F4.SEQ, and *E. coli* JM109 was then transformed with this as described above. The colonies isolated were inoculated into LB medium and incubated as described above. After isolation of the plasmid DNA, restriction digestion was carried out with BglII, with subsequent agarose gel electrophoresis. A clone which showed linearization as evidence of integration of the two oligonucleotides was designated pUC8/UL57/3F and was used for the further cloning work.

c) Restriction digestion was carried out with DNA of the clone pUC8/UL57/3F using BamHI and EcoRI. The fragment of about 200 bp thereby liberated was isolated with the aid of agarose electrophoresis, and was eluted from the piece of gel cut out, as described above. About 50 ng of this DNA fragment were then ligated with 200 ng of the vector pUC8/PCC52/3F, which was opened with BglII and EcoRI and likewise purified by means of electrophoresis. This was followed by transformation with *E. coli* JM109 and plating out onto ampicillin-containing agar plates. The colonies isolated were transferred into 3 ml of LB medium with ampicillin and incubated for 12–16 hours at 37° C., while shaking. After isolation of the plasmid DNA, BamHI/EcoRI restriction digestion was carried out, with subsequent electrophoresis in an agarose gel. A clone with an insert of the expected size was designated pUC8/52/3 UL57/3 and used for the further experiments. The fact that the recognition sequences of BamHI and BglII have the same overhangs, which renders ligation possible, is utilized in this procedure. However, the two cleavage sites are lost after ligation has been carried out. The overhang of 52/3F to UL57/3 is chosen such that translation is possible in the same reading frame.

d) Restriction digestion is carried out with the DNA of the clone pUC8/PCC150/7/2—this clone comprises a part fragment which codes for amino acids 994–1048 of the HCMV antigen pp150—using BamHI and EcoRI. The fragment of about 170 bp thus liberated is purified electrophoretically as described above. 50 ng of the purified fragment are ligated with 200 ng of the vector pUC8/52/3 57/3, treated with BglII and EcoRI, at 4° C. for 16 hours and *E. coli* JM109 is transformed with this. Plating out was carried out onto ampicillin-containing agar plates. The colonies isolated were transferred into 3 ml of LB medium with ampicillin and incubated for 12–16 hours at 37° C., while shaking. After isolation of the plasmid DNA, BamHI/EcoRI restriction digestion was carried out, with subsequent electrophoresis in an agarose gel. A clone with an insert of the expected size was designated pUC8/52/3 57/3 150/7/2 and was used for the further work described herein.

e) To ensure the expression of the autologous fusion protein, recloning of the corresponding DNA fragment into the vector pET5c, which has the strong T7 promoter of gene 10 of bacteriophage T7, was carried out. Upstream of this, this vector has a ribosome binding site and a start codon at an appropriate distance. Behind the start codon lies a reading frame of 11 amino acids of gene 10 of bacteriophage T7 and a BamHI and an EcoRI cleavage site. The reading frame of the BamHI cleavage site coincides with that of the autologous fusion proteins described above. 100 ng of the DNA fragments liberated from pUC8/52/3 UL57/3 and pUC8/52/3 57/3 150/7/2 by means of EcoRI and BamHI restriction digestion were ligated with 200 ng of the vector opened with the same restriction enzymes for 16 hours at 4° C. Transformation with *E. coli* JM109 and plating out onto ampicillin-containing plates then followed. The colonies isolated were transferred into 3 ml of LB medium with ampicillin and incubated for 16 hours at 37° C., while shaking. After isolation of the plasmid DNA, BamHI/EcoRI restriction digestion was carried out. Clones with inserts of the size to be expected were designated pET5a/52/3 UL57/3 and pET5c/52/3 57/3 150/7/2. To ensure expression of the recombinant protein, DNA of the expression clones was transformed into the chloramphenicol-resistant expression strain BL21(DE3)pLysS. One of the resulting clones in each case was used for the further work.

EXAMPLE 11

Chemical Synthesis of the Peptide UL57/3P and its Purification

The peptide UL57/3P was synthesized in accordance with the amino acid sequence shown in FIG. 8 using a Millipore 9050 continuous flow peptide synthesizer (Millipore Corp., Milford, Mass., U.S.A.) using 9-fluorenyl-methoxycarbonyl (Fmoc) chemistry. The synthesis was carried out with 1000 mg of the support material (PEG-PS resin) and 0.8 mmol of the particular activated amino acid ester. Elimination from the support material and removal of the protective groups took place over 12-hours of incubation in a mixture of 88% of trifluoroacetic acid, 5% of phenol (liquid), 2% of triisopropylsilane and 5% of distilled water. Free peptide was precipitated several times with ice-cold ether and then dried in vacuo. Purification was carried out by means of preparative reversed phase HPLC on a C4 column (25×100 mm, 15 μm, 300A, Delta-Pak, Waters, Millipore Corp.) using a gradient of 0–60% acetonitrile in 0.1% TFA). The fractions collected were lyophilized and analyzed by means of reversed phase HPLC and SDS-PAG electrophoresis. Fractions which contained pure peptide were used for the evaluation in ELISA.

EXAMPLE 12

Culture, Expression and Purification of UL57/1-GST, UL57/2-GST and UL57/3-GST 150 ml of LB/AMP medium were inoculated with an isolated colony on an agar plate of the clones pGEX-3/UL57/1-3 (LB/AMP medium). Cultivation was carried out in a liter CF at 37° on a rotary shaker at 160 rpm for 16 hours.

The 3 liter culture was cultured in 6 parallel batches of 0.5 l each in 2 l CF with baffles. The medium LB/CA,AMP) was preheated at 37°. The flasks were inoculated with 20 ml portions of the preculture (1:26) and the batches were incubated at 37° C. and 160 rpm in a rotary shaker. The growth was monitored continuously by measurement of the absorption A at 600 nm. At an A (600 nm) of 0.7, induction was carried out by addition of IPTG (final concentration 1 mM).

Harvesting was carried out 4 h after induction by centrifugation (6×1 l beakers, 4000 g, 0–4°, 30 minutes). The well-drained bacteria pellets were resuspended in 200 ml of ice-cold PBS and centrifuged again (2×250 ml beakers, 5000 g, 0–4°, 10 min). The well-drained pellets were frozen and stored at −20 to −30° C.

After thawing of the bacteria pellets, these were resuspended in 80 ml of base buffer (Tris-HCl/20 mM/pH 7.5) and then homogenized (Teflon/glass Potter homogenizer). The following additives were added, while stirring at room temperature: NP-40 (0.1%), PMSF (0.1 mM), Pefabloc (0.1 mM), EDTA (50 mM) and lysozyme (100 mg). The total volume was 100 ml. The mixture was stirred vigorously at room temperature, and placed on ice after 60 minutes. All the further steps were carried out on ice or with cooling. After the incubation, glycerol (10%) and 2-mercaptoethanol (14 mM) were added and the components were mixed. The volume was brought to 140 ml with base buffer. The lysis mixture was then subjected to ultrasonic treatment (20 kHz, pulsed, 5 minutes, ¾" titanium probe), followed by mechanical Potter treatment (Teflon/glass Potter homogenizer, 1000 rpm, 6 strokes). In the case of the clones pGEX-3/UL57/1 and pGEX/UL57/2, solubilized material was separated off by centrifugation (1×250 ml beaker, 10000 g, 10 minutes, 0–4° C.) and discarded.

In the case of the clone pGEX-3/UL57/3 non-solubilized material was separated off by centrifugation (4×50 ml beakers, 40000 g, 30 minutes, 0–4° C.) and discarded.

The material of the clone pGEX-3/UL57/1 which had not been solubilized after the lysis (pellet) was prehomogenized (Teflon/glass Potter homogenizer) in 50 ml of wash buffer 1 (Tris-HCl/100 mM/pH9/10% glycerol/0.5% NP-40/14 mM 2-mercaptoethanol) and subjected to ultrasonic treatment (20 kHz, pulsed, 5 minutes, ¾" titanium probe). Solubilized material was separated off by centrifugation (2×50 ml beakers, 33000 g, 20 minutes, 0–4° C.) and discarded.

The non-solubilized material (pellets) was prehomogenized (Teflon/glass Potter homogenizer) in 30 ml of wash buffer 2 (glycine-HCl/100 mM/pH3/14 mM 2-mercaptoethanol) and subjected to ultrasonic treatment (20 kHz, pulsed, 5 minutes, ¾" titanium probe). Solubilized material was separated off by centrifugation (1×50 ml beaker, 40000 g, 20 minutes, 0–4° C.) and discarded.

The non-solubilized material (pellet) was prehomogenized (Teflon/glass Potter homogenizer) in 30 ml of wash buffer 3 (Tris-HCl/20 mM/pH9/4 M urea/14 mM 2-mercaptoethanol) and subjected to ultrasonic treatment (20 kHz, pulsed, 5 minutes, ¾" titanium probe). Solubilized material was separated off by centrifugation (1×50 ml beaker, 40000 g, 30 min, 0–4° C.) and discarded.

The insoluble material (pellet) after the 3rd washing step was prehomogenized (Teflon/glass Potter homogenizer) in 30 ml of solubilizing buffer (Tris-HCl/20 mM/pH9/8 M urea/14 mM 2-mercaptoethanol) and subjected to ultrasonic treatment (20 kHz, pulsed, 5 minutes, ¾" titanium probe). Material which continued to be insoluble was separated off by centrifugation (1×50 ml beaker, 40000 g, 30 minutes, 8–10° C.) and discarded.

The solubilized protein was chromatographed on SQ-Sepharose (HiLoad). A column of dimensions 1.6×10 cm (20 ml) was used for this. A (280 nm) and the conductivity were recorded continuously. The flow rate was 5 ml/minute, column buffer=solubilizing buffer. After loading of the sample, followed by 50 ml of column buffer, an initially shallow, linear NaCl gradient (dC/dV=2.5 mM/ml, up to 500 mM) in the column buffer was applied, followed by a steep, linear NaCl gradient (dC/dV=10 mM/ml, up to 1000 mM). The eluate was divided into 10 ml fractions and frozen. The antigen-containing fractions were found in the region of the shallow gradient. Detection was by SDS-PA disk electrophoresis, with subsequent Coomassie staining.

The fractions which were demonstrated as containing pure antigen (Coomassie gel) were thawed, combined and diluted (lowering of the urea concentration to 4 M) with the same volume of renaturing buffer (Tris-HCl/100 mM/pH9/10% glycerol/14 mM 2-mercaptoethanol). All further steps were carried out in a stirred ultrafiltration cell (membrane=Omega 50), while cooling with ice and under a nitrogen atmosphere. The protein solution was first concentrated to about 30 ml and slowly diluted to twice the volume with renaturing buffer. Further concentrations in each case to half the starting volume, followed by dilutions with renaturing buffer in the ratio 1:1, were carried out. The urea concentration was thereby lowered in stages: 4 M–2 M–1 M–0.5 M–0.25 M.

The final concentration of urea was not more than 0.25 M. The retentate was removed from the chamber, and frozen and stored at −60 to −80° C. in aliquot portions.

The material of the clone pGEX-3/UL57/2 which had not been solubilized after the lysis (pellet) was prehomogenized (Teflon/glass Potter homogenizer) in 50 ml of wash buffer 1 (Tris-HCl/100 mM/pH9/10% glycerol/0.5% NP-40/14 mM 2-mercaptoethanol) and subjected to ultrasonic treatment (20 kHz, pulsed, 5 minutes, ¾" titanium probe). Solubilized material was separated off by centrifugation (2×50 ml beakers, 33000 g, 20 minutes, 0–4° C.) and discarded.

The non-solubilized material (pellets) was prehomogenized (Teflon/glass Potter homogenizer) in 30 ml of wash buffer 2 (glycine-HCl/100 mM/pH3/14 mM 2-mercaptoethanol) and subjected to ultrasonic treatment (20 kHz, pulsed, 5 minutes, ¾" titanium probe). Solubilized material was separated off by centrifugation (1×50 ml beaker, 40000 g, 20 minutes, 0–4° C.) and discarded.

The non-solubilized material (pellet) was prehomogenized (Teflon/glass Potter homogenizer) in 30 ml of wash buffer 3 (Tris-HCl/20 mM/pH9/4 M urea/14 mM 2-mercaptoethanol) and subjected to ultrasonic treatment (20 kHz, pulsed, 5 minutes, ¾" titanium probe). Solubilized material was separated off by centrifugation (1×50 ml beaker, 40000 g, 30 minutes, 0–4° C.) and discarded.

The material which was insoluble after the 3rd washing step (pellet) was prehomogenized (Teflon/glass Potter homogenizer) in 30 ml of solubilizing buffer (Tris-HCl/20 mM/pH9/8 M urea/14 mM 2-mercaptoethanol) and subjected to ultrasonic treatment (20 kHz, pulsed, 5 minutes, ¾" titanium probe). Material which continued to be insoluble was separated off by centrifugation (1×50 ml beaker, 40000 g, 30 minutes, 8–10° C.) and discarded.

The solubilized fusion protein was diluted (lowering of the urea concentration to 4 M) with the same volume of renaturing buffer. All further steps were carried out in an ultrafiltration stirred cell (membrane=Omega 50), while cooling with ice and under a nitrogen atmosphere. The protein solution was in each case concentrated to half the starting volume and slowly diluted again with renaturing buffer. The urea concentration was thereby lowered in stages: 4 M–2 M–2 M–0.5 M–0.25 M. The final concentration of urea was not more than 0.25 M. The retentate was removed from the chamber, and frozen and stored at −60 to −80° C. in aliquot portions.

The soluble protein produced by the clone pGEX-3/UL57/3 was chromatographed on GSH-Sepharose-4B (Pharmacia). A column of dimensions 2.6×10 cm (50 ml) was used for this. A (280 nm) was recorded continuously.

The flow rate was 2 ml/minute. Column buffer =Tris-HCl /20 mM/pH7.5/1.4 mM mercaptoethanol. After the sample had been loaded, the column was washed with column buffer until the recorder had reached the base line again. The GST protein was eluted with 5 mM glutathione (GSHred.) in column buffer. The GSH was dissolved immediately before use. The GSH eluate (absorption peak recorded by the recorder) was collected, and frozen and stored at −60 to −80° C. in aliquot portions.

EXAMPLE 13

Culture, Expression and Purification of the Autologous Fusion Protein 52/3 57/3

Starting from a plate colony (LB/CA,AMP) of the clone pET5c 52/3 57/3, a 15 ml culture (LB/CA,AMP) was cultured at 37° C. in a rotary shaker up to an A (600 nm) of 1.8–2.0. The culture was then mixed with glycerol (87%) up to a final concentration of 15% (v/v). The culture was frozen and stored at −60 to −80° C. in 0.1 ml portions.

A frozen aliquot of the preculture was thawed rapidly and pipetted into 150 ml of LB/CA,AMP medium. Cultivation was carried out in a 1 l CF at 28° C. in a rotary shaker at 100 rpm for 16 hours.

The 6 l culture was cultured in 12 parallel batches of 0.5 l each in 2 l CF with baffles. The medium (LB/CA,AMP) was preheated to 37° C. The flasks were inoculated with 10 ml portions of the preculture and incubated at 37° C. and 160 rpm in a rotary shaker. The growth was monitored continuously by measurement of A (600 nm). At an A (600 nm) of 0.6, induction was carried out by addition of IPTG (final concentration 1 mM).

Harvesting was carried out 3 hours after induction by centrifugation (6×1 l beakers, 4000 g, 0–4° C., 30 minutes). The well-drained bacteria pellets were resuspended in 200 ml of ice-cold PBS and centrifuged again (2×250 ml beakers, 5000 g, 0–4° C., 10 minutes). The well-drained pellets were frozen and stored at −20 to −30° C.

The frozen bacteria pellets were thawed and resuspended in 160 ml of base buffer (Tris-HCl/20 mM/pH7.5), and then homogenized with a Teflon/glass Potter homogenizer. The following additives were added, while stirring at room temperature: NP-40 (0.05%), PMSF (0.2 mM), Pefabloc (0.2 mM), EDTA (50 mM) and lysozyme (50 mg). The total volume was 200 ml. After addition of the lysozyme, the mixture was immediately placed on ice. All further steps were carried out on ice or with cooling. After the incubation, glycerol (10%) and 2-mercaptoethanol (14 mM) were added and the components were mixed. The volume was brought to 280 ml with base buffer. The lysis mixture was then subjected to ultrasonic treatment (20 kHz, pulsed, 5 minutes, ¾" titanium probe). Non-solubilized material was removed by centrifugation (2×250 ml beakers, 27000 g, 30 minutes, 0–4° C.). The pellets were discarded.

Solid, finely ground ammonium sulfate was slowly added (in the course of 15 minutes) to the supernatant, while stirring in an ice-bath, up to a concentration of 30% saturation. Stirring was continued for a further 15 minutes. The mixture was then centrifuged (2×250 ml beakers, 27000 g, 30 minutes, 0–4° C.). The pellets were discarded. Ammonium sulfate was added again to the supernatant up to a concentration of 43% saturation, and the mixture was centrifuged as before. The supernatant was discarded. The pellets were resuspended in 25 ml of Tris-HCl/20 mM/pH8.5, which additionally contained 2-mercaptoethanol (14 mM), Pefabloc (0.1 mM) and glycerol (10%), frozen and stored overnight at −20° to −30° C.

The protein solution fractionated with ammonium sulfate (30–43%) was thawed, and precipitated protein was removed by centrifugation (1×50 ml beaker, 40000 g, 30 minutes, 0–4° C.). The supernatant was chromatographed on a Sephadex G-25 (coarse) column (volume at least 200 ml), with A (280 nm) and the conductivity being measured in the flow-through. Column buffer=Tris-HCl/20 mM/pH8.5 with 2-mercaptoethanol (1.4 mM), Pefabloc (0.02 mM) and glycerol (10%). The protein in the exclusion volume was collected in its entirety and further chromatographed directly.

The Sephadex G-25 eluate was chromatographed on SP-Sepharose (Fast Flow). A column of dimensions 2.6×12 cm (60 ml) was used for this. A (280 nm) and the conductivity were recorded continuously. The flow rate was 5 ml/minute. Column buffer=Tris-HCl/20 mM/pH8.5 with 2-mercaptoethanol (1.4 mM), Pefabloc (0.02 mM) and glycerol (10%). After loading of the sample, followed by 100 ml of column buffer, a linear NaCl gradient (dC/dV=1.2 mM/ml, up to 500 mM) in the column buffer was applied. The eluate was divided into 10 ml fractions and frozen. The antigen-containing fractions were in the range between 200 and 300 mM NaCl. Detection was by SDS-PA disk electrophoresis with subsequent Coomassie staining.

The fractions which were demonstrated to contain intact antigen (28.8/27.5 kD bands) (Coomassie gel) were thawed, combined, glycerol was added (20%) and concentration was carried out by ultrafiltration (stirred cell, ice-bath, membrane=Omega 30) to a final volume of about 5 ml. The retentate was removed from the chamber and then chromatographed.

The concentrated SP-Sepharose pool was chromatographed on Superdex 75 (prep grade). A HiLoad column of dimensions 2.6×60 cm (300 ml) was used here. A (280 nm) and the conductivity were recorded continuously. The flow rate was 2 ml/minute. Column buffer=base buffer with NaCl (0.5 M), glycerol (20%), 2-mercaptoethanol (1.4 mM), EDTA (1 mM), PMSF (0.1 mM) and Pefabloc (0.02 mM). The eluate was divided into 5 ml fractions and frozen. The antigen-containing fractions were in the 2nd absorption peak. Detection was by SDS-PA disk electrophoresis with subsequent Coomassie staining.

The fractions which were demonstrated to contain intact and pure antigen (Coomassie gel) were thawed, combined and concentrated by means of ultrafiltration (stirred cell, ice-bath, membrane=Omega 30) to a final concentration of at least 2 mg/ml. The retentate was removed from the chamber, and frozen and stored at −60 to −80° C. in aliquot portions.

EXAMPLE 14

Culture, Expression and Purification of the Autologous Fusion Protein 52/3 57/3 150/7/2

The culture and lysis were carried out as described for the autologous fusion protein 52/3 57/3.

Solid, finely ground ammonium sulfate was slowly added (in the course of 15 minutes) to the supernatant obtained after the lysis, while stirring in an ice-bath, up to a concentration of 30% saturation. Stirring was continued for a further 15 minutes. The mixture was then centrifuged (2×250 ml beakers, 27000 g, 30 minutes, 0–4° C.). The pellets were discarded. Ammonium sulfate was added again to the supernatant up to a concentration of 38% saturation, and the mixture was centrifuged as before. The supernatant was discarded. The pellets were resuspended in 25 ml of Tris-HCl/20 mM/pH9 buffer, which additionally contained 2-mercaptoethanol (14 mM), Pefabloc (0.1 mM) and glycerol (10%), frozen and stored overnight at −20° to −30° C.

The protein solution fractionated with ammonium sulfate (30–38%) was thawed, and precipitated protein was removed by centrifugation (1×50 ml beaker, 40000 g, 30 minutes, 0–4° C.). The supernatant was chromatographed on a Sephadex G-25 (coarse) column (volume at least 200 ml), with A (280 nm) and the conductivity being measured in the flow-through. Column buffer=Tris-HCl/20 mM/pH9 with 2-mercaptoethanol (1.4 mM), Pefabloc (0.02 mM) and glycerol (10%). The protein in the exclusion volume was collected in its entirety and further chromatographed directly.

The Sephadex G-25 eluate was chromatographed on SP-Sepharose (Fast Flow). A column of dimensions 2.6×12 cm (60 ml) was used for this. A (280 nm) and the conductivity were recorded continuously. The flow rate was 5 ml/minute. Column buffer=Tris-HCl/20 mM/pH9 with 2-mercaptoethanol (1.4 mM), Pefabloc (0.02 mM) and glycerol (10%). After loading of the sample, followed by 100 ml of column buffer, a linear NaCl gradient (dC/dV=1.7 mM/ml, up to 500 mM) in the column buffer was applied. The eluate was divided into 10 ml fractions and frozen. The antigen-containing fractions were in the range between 150 and 300 mM NaCl. Detection was by SDS-PA disk electrophoresis with subsequent Coomassie staining.

The fractions which were demonstrated to contain intact antigen (33 kD band) (Coomassie gel) were thawed, combined, glycerol was added (20%) and concentration carried out by ultrafiltration (stirred cell, ice-bath, membrane=Omega 30) to a final volume of about 5 ml. The retentate was removed from the chamber and then chromatographed.

The concentrated SP-Sepharose pool was chromatographed on Superdex 75 (prep grade). A HiLoad column of dimensions 2.6×60 cm (300 ml) was used here. A (280 nm) and the conductivity were recorded continuously. The flow rate was 2 ml/minute. Column buffer=base buffer with NaCl (0.5 M), glycerol (20%), 2-mercaptoethanol (1.4 mM), EDTA (1 mM), PMSF (0.1 mM) and Pefabloc (0.02 mM). The eluate was divided into 5 ml fractions and frozen. The antigen-containing fractions were in the first absorption peak (=largest peak). Detection was by SDS-PA disk electrophoresis with subsequent Coomassie staining.

The fractions which were demonstrated to contain intact and pure antigen (Coomassie gel) were thawed, combined and concentrated by means of ultrafiltration (stirred cell, ice-bath, membrane=Omega 30) to a final concentration of at least 2 mg/ml. The retentate was removed from the chamber, and frozen and stored at −60 to −80° C. in aliquot portions.

EXAMPLE 15

Evaluation of the Recombinant Antigens in ELISA 100 ng portions of the purified recombinant antigens UL57/1, UL57/3 and 52/3 UL57/3 and 200 ng portions of the antigens UL57/2 and 52/3 57/3 150/7/2 were dissolved in 100 μl portions of 0.01 M carbonate buffer, pH 9.5, and the solutions were introduced into the wells of microtiter plates (Polycorb, Nunc) and incubated for 16 hours in an earthed humidity chamber. After addition of 100 μl of a second coating solution comprising calf serum, incubation was continued for a further 2 hours. The plates were then emptied and carefully tapped out. The plates were then used for the actual test procedure or, after drying in a vacuum cabinet and subsequent sealing into tubular film, were stored at −20° C. until used later. Coating of the chemically synthesized peptide was carried out with 2 μg/100 μl as described above, using Maxisorb ELISA plates (Nunc). For the actual test procedure, the test wells of the ELISA plates were filled with 100 μl of serum diluted 1:21, sealed off with a plastic film and incubated for 1 hour at 40° C. floating in a water-bath. After washing three times in a Biotest ELISA Washer II, incubation was carried out with 100 μl of a peroxidase-labeled monoclonal mouse antibody directed against human IgM (Janssen) for 30 minutes at 40° C. After renewed washing, the antibodies bound were visualized by a color reaction with 1,2-phenylenediamine as the chromogen. The optical density of the individual sample was determined at 495 nm (reference: 620 nm) on an Anthos HTII ELISA reader. All OD values greater than 0.3 were evaluated as a positive result.

The results of the evaluations thus obtained are shown in Tables 3–5.

TABLE 1

IgM reactivity of the recombinant antigens with sera of healthy blood donors

| | Total positive (OD > 0.3) | OD < 0.5 | OD 0.5 < 1.0 | OD > 1.0 |
|---|---|---|---|---|
| A: CMV-seropositive (n = 54) | | | | |
| 150/7 | 19 | 7 | 8 | 4 |
| 52/3 | 1 | — | 1 | — |
| 52/3\|105/7/2 | 1 | — | 1 | — |
| B: CMV-seronegative (n = 54) | | | | |
| 150/7 | — | — | — | — |
| 52/3 | — | — | — | — |
| 52/3\|150/7/2 | — | — | — | — |

FIG. 5

TABLE 2

OD Values in IgM ELISA with sera of immunocompetent patients with an acute HCMV infection. The shaded values are above the cut-off of 0.3.

| Serum | 150/7 | 52/3 | 52/3\|150/7/2 |
|---|---|---|---|
| 75332 | 1.576 | 0.353 | 0.736 |
| 81297 | 3.0 | 0.533 | 1.494 |
| 83381 | 3.0 | 0.971 | 1.684 |
| 103850 | 2.473 | 0.305 | 3.189 |
| 112690 | 0.411 | 0.077 | 0.167 |
| 132847 | 1.268 | 0.249 | 0.111 |
| 138076 | 3.0 | 2.019 | 2.518 |
| 145608 | 0.289 | 1.863 | 2.493 |
| 65327 | 1.448 | 0.282 | 1.140 |
| 0162 | 2.742 | 0.203 | 1.434 |
| 1012 | 2.736 | 0.139 | 1.506 |
| 9344 | 2.689 | 0.065 | 2.180 |
| 1744 | 2.427 | 0.030 | 1.704 |
| 1150 | 3.0 | 0.258 | 1.355 |
| 3313 | 3.0 | 0.165 | 0.542 |

FIG. 6

TABLE 3

IgM reactivity with selected sera of immunocompetent individuals with an acute HCMV infection, detected by seroconversion and by isolation of CMV from the blood or urine

| | | Reference antigens | | GST Fusion | | Autologous Fusion | | | |
|---|---|---|---|---|---|---|---|---|---|
| Patient No | Reference test IgM[1] | 150/7 | 52/3 | UL57/1 | UL57/2 | 52/3 57/3 | 52/3 57/3 150/7/2 | UL57/3P | |
| 1 | 5.7 | 1.576 | 0.353 | 0.014 | 0.030 | 3.0 | 0.355 | 0.993 | 0.863 |
| 2 | 6.0 | 0.019 | 0.166 | 0.057 | 0.147 | 3.0 | 3.0 | 3.0 | 3.0 |
| 3 | 1.0 | 3.0 | 0.533 | 0.085 | 0.179 | 0.896 | 0.417 | 1.733 | 0.058 |
| 4 | 7.4 | 3.0 | 0.971 | 0.036 | 0.092 | 0.546 | 1.110 | 3.0 | 0.090 |
| 5 | 7.4 | 2.473 | 0.305 | 0.392 | 0.488 | 3.0 | 2.387 | 2.096 | 0.413 |
| 6 | 5.2 | 0.692 | 0.383 | 0.007 | 0.016 | 1.413 | 0.896 | 0.578 | 0.403 |
| 7 | 5.3 | 0.411 | 0.077 | 0.043 | 0.039 | 3.0 | 0.704 | 0.941 | 0.688 |
| 8 | 3.8 | 0.764 | 0.533 | 0.020 | 0.037 | 0.658 | 0.732 | 0.783 | 0.138 |
| 9 | 4.2 | 1.268 | 0.249 | 0.053 | 0.042 | 3.0 | 0.592 | 0.413 | 0.325 |
| 10 | 5.8 | 1.470 | 1.413 | 0.086 | 0.198 | 3.0 | 2.626 | 2.360 | 2.049 |
| 11a 14.8.92 | 2.0 | 3.0 | 0.545 | 0.016 | 0.077 | 3.0 | 0.897 | 0.831 | 0.714 |
| 11b 1.9.92 | 6.0 | 3.0 | 2.019 | 0.061 | 0.118 | 3.0 | 3.0 | 2.700 | 2.802 |
| 12 | 2.1 | 0.289 | 1.863 | 0.052 | 0.231 | 3.0 | 3.0 | 2.778 | 2.318 |
| 13 | nd. | 2.188 | 1.740 | 0.082 | 0.207 | 1.740 | 1.345 | 2.360 | 1.444 |
| Σ 14 | above cut-off: | 13 | 12 | 1 | 1 | 14 | 14 | 14 | 11 |

[1] sample/cut-off ratio (Medac IgM)

▓ = Results above the provisionally specified cut-off of OD 0.3

FIG. 11

TABLE 4

IgM reactivity with selected sera of transplant patients with an acute HCMV primary infection. The sera were taken 2–3 weeks after the start of the antigenemia.

| Patient No | Positive cells/ 50000 Antigenemia | Reference antigens | | GST Fusion | | | Autologous Fusion | | UL57/3P |
|---|---|---|---|---|---|---|---|---|---|
| | | 150/7 | 52/3 | UL57/1 | UL57/2 | UL57/3 | 52/3 57/3 | 52/3 57/3 150/7/2 | |
| 1 | 13 | 1.998 | 0.771 | 0.024 | 0.064 | 3.0 | 1.535 | 1.750 | 1.394 |
| 2 | 113 | 0.220 | 0.191 | 0.103 | 0.031 | 0.273 | 0.171 | 0.188 | 0.030 |
| 3 | 15 | 2.643 | 1.186 | 0.021 | 0.037 | 2.051 | 1.397 | 1.458 | 0.925 |
| 4 | 30 | 1.660 | 0.878 | 0.127 | 0.234 | 1.034 | 0.821 | 0.891 | 0.418 |
| 5 | 0 | 2.761 | 1.936 | 0.040 | 0.149 | 3.0 | 3.0 | 3.0 | 3.0 |
| 6 | 135 | 1.768 | 0.993 | 0.813 | 0.123 | 2.697 | 2.742 | 2.352 | 2.662 |
| 7 | 25 | 2.703 | 2.259 | 0.679 | 0.271 | 3.0 | 3.0 | 2.830 | 3.0 |
| 8 | 7 | 0.987 | 0.806 | 0.038 | 0.071 | 2.773 | 1.879 | 0.951 | 1.088 |
| 9 | 40 | 3.0 | 0.404 | 0.069 | 0.087 | 0.980 | 0.688 | 1.803 | 0.135 |
| Σ 9 | above cut-off: | 8 | 8 | 2 | — | 8 | 8 | 8 | 7 |

▓ = Results above the provisionally specified cut-off of OD 0.3

FIG. 12

TABLE 5

IgM Reactivity of the recombinant antigens with sera of healthy blood donors

| | | 150/7 | 52/3 | UL57/ 1-GST | UL57/ 2-GST | UL57/ 3-GST | 52/3 57/3 | 52/3 57/3 150/7/2 | UL57/ 3P |
|---|---|---|---|---|---|---|---|---|---|
| A. | CMV-seropositive blood donors n = 54 | 19 | 1 | — | — | 1 | 1 | 2 | 1 |
| B. | CMV-seronegative blood donors n = 54 | — | — | — | — | 1 | — | — | — |

FIG. 13

TABLE 6

Brief characterization of the antigens evaluated

| Antigen | Characterization | Reading frame Amino acid range | Diagnostic importance |
|---|---|---|---|
| UL57/1-GST | GST fusion protein | UL57 aa 755–1000 | − |
| UL57/2-GST | GST fusion protein | UL57 aa 1144–1196 | − |
| UL57/3-GST | GST fusion protein | UL57 aa 545–601 | +++ |
| UL57/3-P | Peptide | UL57 aa 545–601 | ++ |
| 52/53 57/3 | Autologous fusion protein | UL44 aa 297–433 + UL57 aa 545 601 | +++ |
| 52/3 57/3 150/7/2 | Autologous fusion protein | UL44 aa 297–433 + UL57 aa 545–601 + UL32 aa 994–1048 | +++ |

FIG. 14

SEQUENCE LISTING (1) GENERAL INFORMATION:

(iii) NUMBER OF SEQUENCES: 26

(2) INFORMATION FOR SEQ ID NO: 1:

(i) SEQUENCE CHARACTERISTICS:
       (A) LENGTH: 57 amino acids
       (B) TYPE: amino acid
       (C) STRANDEDNESS: single
       (D) TOPOLOGY: linear (ii) MOLECULE TYPE: Protein (v) FRAGMENT TYPE: internal (xi) SEQUENCE DESCRIPTION: SEQ ID NO: 1:

Gly Val Pro Gly Gly Gly Ala Gly Gly Gly Gly Arg Asp Val Ser
1               5                   10                  15

Gly Gly Pro Ser Asp Gly Leu Gly Gly Arg Gly Gly Gly Gly
            20                  25                  30

Gly Asp Ser Gly Gly Met Met Gly Arg Gly Gly Arg Met Leu Gly Ala
        35                  40                  45

Ser Val Asp Arg Thr Tyr Arg Leu Asn
    50                  55

(2) INFORMATION FOR SEQ ID NO: 2:

(i) SEQUENCE CHARACTERISTICS:
       (A) LENGTH: 27 base pairs
       (B) TYPE: nucleic acid
       (C) STRANDEDNESS: single
       (D) TOPOLOGY: linear (ii) MOLECULE TYPE: Primer DNA (xi) SEQUENCE DESCRIPTION: SEQ ID NO: 2:

GAATTCTATT CCTCCGTGTT CTTAATC                                   27

(2) INFORMATION FOR SEQ ID NO: 3:

(i) SEQUENCE CHARACTERISTICS:
       (A) LENGTH: 26 base pairs
       (B) TYPE: nucleic acid
       (C) STRANDEDNESS: single
       (D) TOPOLOGY: linear (ii) MOLECULE TYPE: Primer DNA (xi) SEQUENCE DESCRIPTION: SEQ ID NO: 3:

CGGATCCTGA AGAGCACGAC GGGCAT                                    26

(2) INFORMATION FOR SEQ ID NO: 4:

(i) SEQUENCE CHARACTERISTICS:
       (A) LENGTH: 35 base pairs
       (B) TYPE: nucleic acid
       (C) STRANDEDNESS: single
       (D) TOPOLOGY: linear (ii) MOLECULE TYPE: Primer DNA (xi) SEQUENCE DESCRIPTION: SEQ ID NO: 4:

GGATCCGCAT GCGTGGCAGC CTCTCTTCGC TGGCC                          35

(2) INFORMATION FOR SEQ ID NO: 5:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: Primer DNA (xi) SEQUENCE DESCRIPTION: SEQ ID NO: 5:

```
GAATTCAGAT CTTGCCGCAC TTTTGCTTCT                                         30
```

(2) INFORMATION FOR SEQ ID NO: 6:

(i) SEQUENCE CHARACTERISTICS:
        (A) LENGTH: 607 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 6:

```
GGATCCGCAT GCGTGGCAGC CTCTCTTCGC TGGCCAATGC CGGCGGTCTG CATGACGACG         60
GCCCGGGTCT GGATAACGAT CTCATGAACG AGCCCATGGG TCTCGGCGGT CTGGGAGGAG        120
GTGGCGGCGG TGGCGGCAAG AAGCACGACC GCGGTGGCGG CGGTGGTTCC GGTACGCGGA        180
AAATGAGTAG CGGTGGCGGC GGCGGTGATC ATGACCACGG TCTTTCCTCC AAGGAAAAAT        240
ACGAGCAGCA CAAGATCACC AGCTACCTGA CGTCCAAAGG TGGATCGGGC GGCGGCGGAG        300
GAGGAGGAGG CGGCGGTTTG GATCGCAACT CCGGCAATTA CTTCAACGAC GCGAAAGAGG        360
AGAGCGACAG CGAGGATTCT GTAACGTTCG AGTTCGTCCC TAACACCAAG AAGCAAAAGT        420
GCGGCAAGAT CCTGAAGAGC ACGACGGGCA TGAAAACGGT GGCTTTCGAC CTATCGTCGC        480
CCCAGAAGAG CGGTACGGGG CCGCAACCGG GTTCTGCCGG CATGGGGGGC GCCAAAACGC        540
CGTCGGACGC CGTGCAGAAC ATCCTCCAAA AGATCGAGAA GATTAAGAAC ACGGAGGAAT        600
AGAATTC                                                                 607
```

(2) INFORMATION FOR SEQ ID NO: 7:

(i) SEQUENCE CHARACTERISTICS:
        (A) LENGTH: 607 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 7:

```
CCTAGGCGTA CGCACCGTCG GAGAGAAGCG ACCGGTTACG GCCGCCAGAC GTACTGCTGC         60
CGGGCCCAGA CCTATTGCTA GAGTACTTGC TCGGGTACCC AGAGCCGCCA GACCCTCCTC        120
CACCGCCGCC ACCGCCGTTC TTCGTGCTGG CGCCACCGCC GCCACCAAGG CCATGCGCCT        180
TTTACTCATC GCCACCGCCG CCGCCACTAG TACTGGTGCC AGAAAGGAGG TTCCTTTTTA        240
TGCTCGTCGT GTTCTAGTGG TCGATGGACT GCAGGTTTCC ACCTAGCCCG CCGCCGCCTC        300
CTCCTCCTCC GCCGCCAAAC CTAGCGTTGA GGCCGTTAAT GAAGTTGCTG CGCTTTCTCC        360
TCTCGCTGTC GCTCCTAAGA CATTGCAAGC TCAAGCAGGG ATTGTGGTTC TTCGTTTTCA        420
CGCCGTTCTA GGACTTCTCG TGCTGCCCGT ACTTTTGCCA CCGAAAGCTG GATAGCAGCG        480
```

```
GGGTCTTCTC GCCATGCCCC GGCGTTGGCC CAAGACGGCC GTACCCCCG CGGTTTTGCG      540

GCAGCCTGCG GCACGTCTTG TAGGAGGTTT TCTAGCTCTT CTAATTCTTG TGCCTCCTTA      600

TCTTAAG                                                                607
```

(2) INFORMATION FOR SEQ ID NO: 8:

(i) SEQUENCE CHARACTERISTICS:
        (A) LENGTH: 199 amino acids
        (B) TYPE: amino acid
        (C) STRANDEDNESS: single
        (D) TOPOLOGY: linear (ii) MOLECULE TYPE: Protein (v) FRAGMENT TYPE: internal (xi) SEQUENCE DESCRIPTION: SEQ ID NO: 8:

```
Ile Arg Met Arg Gly Ser Leu Ser Ser Leu Ala Asn Ala Gly Gly Leu
1               5                   10                  15

His Asp Asp Gly Pro Gly Leu Asp Asn Asp Leu Met Asn Glu Pro Met
                20                  25                  30

Gly Leu Gly Gly Leu Gly Gly Gly Gly Gly Gly Gly Lys Lys His
            35                  40                  45

Asp Arg Gly Gly Gly Gly Ser Gly Thr Arg Lys Met Ser Ser Gly
        50                  55                  60

Gly Gly Gly Asp His Asp His Gly Leu Ser Ser Lys Glu Lys Tyr
65                  70                  75                  80

Glu Gln His Lys Ile Thr Ser Tyr Leu Thr Ser Lys Gly Ser Gly
                85                  90                  95

Gly Gly Gly Gly Gly Gly Gly Leu Asp Arg Asn Ser Gly Asn
            100                 105                 110

Tyr Phe Asn Asp Ala Lys Glu Glu Ser Asp Ser Glu Asp Ser Val Thr
                115                 120                 125

Phe Glu Phe Val Pro Asn Thr Lys Lys Gln Lys Cys Gly Lys Ile Leu
            130                 135                 140

Lys Ser Thr Thr Gly Met Lys Thr Val Ala Phe Asp Leu Ser Ser Pro
145                 150                 155                 160

Gln Lys Ser Gly Thr Gly Pro Gln Pro Gly Ser Ala Gly Met Gly Gly
                165                 170                 175

Ala Lys Thr Pro Ser Asp Ala Val Gln Asn Ile Leu Gln Lys Ile Glu
                180                 185                 190

Lys Ile Lys Asn Thr Glu Glu
            195
```

(2) INFORMATION FOR SEQ ID NO: 9:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: Primer DNA (xi) SEQUENCE DESCRIPTION: SEQ ID NO: 9:

```
GGATCCGCAT GCATCACGAC CGCCTGCTGG ACT                                    33
```

(2) INFORMATION FOR SEQ ID NO: 10:

(i) SEQUENCE CHARACTERISTICS:

```
          (A) LENGTH: 29 base pairs
          (B) TYPE: nucleic acid
          (C) STRANDEDNESS: single
          (D) TOPOLOGY: linear (ii) MOLECULE TYPE: Primer DNA (xi) SEQUENCE DESCRIPTION: SEQ ID NO: 10:

GAATTCTTAG TTGTTGATAC CCGCATATT                              29

(2) INFORMATION FOR SEQ ID NO: 11:

(i) SEQUENCE CHARACTERISTICS:
          (A) LENGTH: 34 base pairs
          (B) TYPE: nucleic acid
          (C) STRANDEDNESS: single
          (D) TOPOLOGY: linear (ii) MOLECULE TYPE: Primer DNA (xi) SEQUENCE DESCRIPTION: SEQ ID NO: 11:

GGATCCGCAT GCATGGGGTT CCGGGCGGCG GTGC                         34

(2) INFORMATION FOR SEQ ID NO: 12:

(i) SEQUENCE CHARACTERISTICS:
          (A) LENGTH: 31 base pairs
          (B) TYPE: nucleic acid
          (C) STRANDEDNESS: single
          (D) TOPOLOGY: linear (ii) MOLECULE TYPE: Primer DNA (xi) SEQUENCE DESCRIPTION: SEQ ID NO: 12:

GAATTCTCTA GAATTGAGCC GATAGGTACG G                            31

(2) INFORMATION FOR SEQ ID NO: 13:

(i) SEQUENCE CHARACTERISTICS:
          (A) LENGTH: 42 base pairs
          (B) TYPE: nucleic acid
          (C) STRANDEDNESS: single
          (D) TOPOLOGY: linear (ii) MOLECULE TYPE: Primer DNA (xi) SEQUENCE DESCRIPTION: SEQ ID NO: 13:

GATCCCCTCT AGAGACGCTC AGCGTCTTAC TGACGCTGCA GG                42

(2) INFORMATION FOR SEQ ID NO: 14:

(i) SEQUENCE CHARACTERISTICS:
          (A) LENGTH: 42 base pairs
          (B) TYPE: nucleic acid
          (C) STRANDEDNESS: single
          (D) TOPOLOGY: linear (ii) MOLECULE TYPE: Primer DNA (xi) SEQUENCE DESCRIPTION: SEQ ID NO: 14:

AATCTCTGCA GCGTCAGTAA GACGCTGAGC GTCTCTAGAG GG                42

(2) INFORMATION FOR SEQ ID NO: 15:

(i) SEQUENCE CHARACTERISTICS:
          (A) LENGTH: 72 base pairs
          (B) TYPE: nucleic acid
          (C) STRANDEDNESS: single
          (D) TOPOLOGY: linear
```

(ii) MOLECULE TYPE: Primer DNA (xi) SEQUENCE DESCRIPTION: SEQ ID NO: 15:

GGTGGTGAAG TTCATGACCT TTCTGCTCTT TTCGCTCCGT CTGGTGTTGG TGCAGCTTCT    60

GGTGTTGGTG GG                                                       72

(2) INFORMATION FOR SEQ ID NO: 16:

(i) SEQUENCE CHARACTERISTICS:
            (A) LENGTH: 80 base pairs
            (B) TYPE: nucleic acid
            (C) STRANDEDNESS: single
            (D) TOPOLOGY: linear (ii) MOLECULE TYPE: Primer DNA (xi) SEQUENCE DESCRIPTION: SEQ ID NO: 16:

AATCTCCACC AACACCAGAA GCTGCACCAA CACCAGACGG AGCGAAAAGA GCAGAAAGGT    60

CATGAACTTC ACCACCTGCA                                               80

(2) INFORMATION FOR SEQ ID NO: 17:

(i) SEQUENCE CHARACTERISTICS:
            (A) LENGTH: 61 base pairs
            (B) TYPE: nucleic acid
            (C) STRANDEDNESS: single
            (D) TOPOLOGY: linear (ii) MOLECULE TYPE: Primer DNA (xi) SEQUENCE DESCRIPTION: SEQ ID NO: 17:

TGGTGGTCTG CTTCTTGGTG AATCTGTTGC TGGTAACTCT ATCTGCTTCG GTGTCCCGGG    60

G                                                                   61

(2) INFORMATION FOR SEQ ID NO: 18:

(i) SEQUENCE CHARACTERISTICS:
            (A) LENGTH: 67 base pairs
            (B) TYPE: nucleic acid
            (C) STRANDEDNESS: single
            (D) TOPOLOGY: linear (ii) MOLECULE TYPE: Primer DNA (xi) SEQUENCE DESCRIPTION: SEQ ID NO: 18:

AATTCCCCGG GACACCGAAG CAGATAGAGT TACCAGCAAC AGATTCACCA AGAAGCAGAC    60

CACCACC                                                             67

(2) INFORMATION FOR SEQ ID NO: 19:

(i) SEQUENCE CHARACTERISTICS:
            (A) LENGTH: 171 base pairs
            (B) TYPE: nucleic acid
            (C) STRANDEDNESS: single
            (D) TOPOLOGY: linear (ii) MOLECULE TYPE: Genomic DNA (xi) SEQUENCE DESCRIPTION: SEQ ID NO: 19:

GGGGTTCCGG GCGGCGGTGC TGGCGGGGGT GGTGGACGAG ACGTGAGCGG GGGCCCGAGC    60

GACGGTCTGG GTGGCGGTCG TGGTGGTGGG GGTGGTGGGG ATTCCGGGGG AATGATGGGG   120

CGCGGCGGTC GCATGTTGGG CGCTAGCGTG GACCGTACCT ATCGGCTCAA T            171

(2) INFORMATION FOR SEQ ID NO: 20:

(i) SEQUENCE CHARACTERISTICS:
(A) LENGTH: 171 base pairs
(B) TYPE: nucleic acid
(C) STRANDEDNESS: single
(D) TOPOLOGY: linear (ii) MOLECULE TYPE: Genomic DNA (xi) SEQUENCE DESCRIPTION: SEQ ID NO: 20:

```
CCCCAAGGCC CGCCGCCACG ACCGCCCCCA CCACCTGCTC TGCACTCGCC CCCGGGCTCG      60
CTGCCAGACC CACCGCCAGC ACCACCACCC CCACCACCCC TAAGGCCCCC TTACTACCCC     120
GCGCCGCCAG CGTACAACCC GCGATCGCAC CTGGCATGGA TAGCCGAGTT A              171
```

(2) INFORMATION FOR SEQ ID NO: 21:

(i) SEQUENCE CHARACTERISTICS:
(A) LENGTH: 651 base pairs
(B) TYPE: nucleic acid
(C) STRANDEDNESS: single
(D) TOPOLOGY: linear (ii) MOLECULE TYPE: Genomic DNA (xi) SEQUENCE DESCRIPTION: SEQ ID NO: 21:

```
ATGGCTAGCA TGACTGGTGG ACAGCAAATG GGTCGCCGGA TCCGCATGCG TGGCAGCCTC      60
TCTTCGCTGG CCAATGCCGG CGGTCTGCAT GACGACGGCC CGGGTCTGGA TAACGATCTC     120
ATGAACGAGC CCATGGGTCT CGGCGGTCTG GGAGGAGGTG GCGGCGGTGG CGGCAAGAAG     180
CACGACCGCG GTGGCGGCGG TGGTTCCGGT ACGCGGAAAA TGAGTAGCGG TGGCGGCGGC     240
GGTGATCATG ACCACGGTCT TTCCTCCAAG GAAAAATACG AGCAGCACAA GATCACCAGC     300
TACCTGACGT CCAAAGGTGG ATCGGGCGGC GGCGGAGGAG GAGGAGGCGG CGGTTTGGAT     360
CGCAACTCCG GCAATTACTT CAACGACGCG AAAGAGGAGA GCGACAGCGA GGATTCTGTA     420
ACGTTCGAGT TCGTCCCTAA CACCAAGAAG CAAAAGTGCG GCAAGATCCG CATGCATGGG     480
GTTCCGGGCG GCGGTGCTGG CGGGGGTGGT GGACGAGACG TGAGCGGGGG CCCGAGCGAC     540
GGTCTGGGTG GCGGTCGTGG TGGTGGGGGT GGTGGGGATT CCGGGGGAAT GATGGGGCGC     600
GGCGGTCGCA TGTTGGGCGC TAGCGTGGAC CGTACCTATC GGCTCAATTA G              651
```

(2) INFORMATION FOR SEQ ID NO: 22:

(i) SEQUENCE CHARACTERISTICS:
(A) LENGTH: 651 base pairs
(B) TYPE: nucleic acid
(C) STRANDEDNESS: single
(D) TOPOLOGY: linear (ii) MOLECULE TYPE: Genomic DNA (xi) SEQUENCE DESCRIPTION: SEQ ID NO: 22:

```
TACCGATCGT ACTGACCACC TGTCGTTTAC CCAGCGGCCT AGGCGTACGC ACCGTCGGAG      60
AGAAGCGACC GGTTACGGCC GCCAGACGTA CTGCTGCCGG GCCCAGACCT ATTGCTAGAG     120
TACTTGCTCG GTACCCAGA GCCGCCAGAC CCTCCTCCAC CGCCGCCACC GCCGTTCTTC      180
GTGCTGGCGC CACCGCCGCC ACCAAGGCCA TGCGCCTTTT ACTCATCGCC ACCGCCGCCG     240
CCACTAGTAC TGGTGCCAGA AAGGAGGTTC CTTTTTATGC TCGTCGTGTT CTAGTGGTCG     300
ATGGACTGCA GGTTTCCACC TAGCCCGCCG CCGCCTCCTC CTCCTCCGCC GCCAAACCTA     360
```

```
GCGTTGAGGC CGTTAATGAA GTTGCTGCGC TTTCTCCTCT CGCTGTCGCT CCTAAGACAT    420

TGCAAGCTCA AGCAGGGATT GTGGTTCTTC GTTTTCACGC CGTTCTAGGC GTACGTACCC    480

CAAGGCCCGC CGCCACGACC GCCCCCACCA CCTGCTCTGC ACTCGCCCCC GGGCTCGCTG    540

CCAGACCCAC CGCCAGCACC ACCACCCCCA CCACCCCTAA GGCCCCCTTA CTACCCCGCG    600

CCGCCAGCGT ACAACCCGCG ATCGCACCTG GCATGGATAG CCGAGTTAAT C             651
```

(2) INFORMATION FOR SEQ ID NO: 23:

(i) SEQUENCE CHARACTERISTICS:
        (A) LENGTH: 216 amino acids
        (B) TYPE: amino acid
        (C) STRANDEDNESS: single
        (D) TOPOLOGY: linear (ii) MOLECULE TYPE: Polypeptide (v) FRAGMENT TYPE: internal (xi) SEQUENCE DESCRIPTION: SEQ ID NO: 23:

```
Met Ala Ser Met Thr Gly Gly Gln Gln Met Gly Arg Arg Ile Arg Met
 1               5                  10                  15

Arg Gly Ser Leu Ser Ser Leu Ala Asn Ala Gly Gly Leu His Asp Asp
                20                  25                  30

Gly Pro Gly Leu Asp Asn Asp Leu Met Asn Glu Pro Met Gly Leu Gly
            35                  40                  45

Gly Leu Gly Gly Gly Gly Gly Gly Gly Lys Lys His Asp Arg Gly
    50                  55                  60

Gly Gly Gly Gly Ser Gly Thr Arg Lys Met Ser Ser Gly Gly Gly
65                  70                  75                  80

Gly Asp His Asp His Gly Leu Ser Ser Lys Glu Lys Tyr Glu Gln His
                85                  90                  95

Lys Ile Thr Ser Tyr Leu Thr Ser Lys Gly Gly Ser Gly Gly Gly
                100                 105                 110

Gly Gly Gly Gly Gly Gly Leu Asp Arg Asn Ser Gly Asn Tyr Phe Asn
            115                 120                 125

Asp Ala Lys Glu Glu Ser Asp Ser Glu Asp Ser Val Thr Phe Glu Phe
130                 135                 140

Val Pro Asn Thr Lys Lys Gln Lys Cys Gly Lys Ile Arg Met His Gly
145                 150                 155                 160

Val Pro Gly Gly Gly Ala Gly Gly Gly Gly Arg Asp Val Ser Gly
                165                 170                 175

Gly Pro Ser Asp Gly Leu Gly Gly Gly Arg Gly Gly Gly Gly Gly
            180                 185                 190

Asp Ser Gly Gly Met Met Gly Arg Gly Gly Arg Met Leu Gly Ala Ser
            195                 200                 205

Val Asp Arg Thr Tyr Arg Leu Asn
            210                 215
```

(2) INFORMATION FOR SEQ ID NO: 24:

(i) SEQUENCE CHARACTERISTICS:
        (A) LENGTH: 831 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 24:

```
ATGGCTAGCA TGACTGGTGG ACAGCAAATG GGTCGCCGGA TCCGCATGCG TGGCAGCCTC      60

TCTTCGCTGG CCAATGCCGG CGGTCTGCAT GACGACGGCC CGGGTCTGGA TAACGATCTC     120

ATGAACGAGC CCATGGGTCT CGGCGGTCTG GGAGGAGGTG GCGGCGGTGG CGGCAAGAAG     180

CACGACCGCG GTGGCGGCGG TGGTTCCGGT ACGCGGAAAA TGAGTAGCGG TGGCGGCGGC     240

GGTGATCATG ACCACGGTCT TTCCTCCAAG GAAAAATACG AGCAGCACAA GATCACCAGC     300

TACCTGACGT CCAAAGGTGG ATCGGGCGGC GGCGGAGGAG GAGGAGGCGG CGGTTTGGAT     360

CGCAACTCCG GCAATTACTT CAACGACGCG AAAGAGGAGA GCGACAGCGA GGATTCTGTA     420

ACGTTCGAGT TCGTCCCTAA CACCAAGAAG CAAAAGTGCG GCAAGATCCG CATGCATGGG     480

GTTCCGGGCG GCGGTGCTGG CGGGGGTGGT GGACGAGACG TGAGCGGGGG CCCGAGCGAC     540

GGTCTGGGTG GCGGTCGTGG TGGTGGGGGT GGTGGGGATT CCGGGGGAAT GATGGGGCGC     600

GGCGGTCGCA TGTTGGGCGC TAGCGTGGAC CGTACCTATC GGCTCAATTC TAGAAAGATC     660

CTGAAGAGCA CGACGGGCAT GAAAACGGTG GCTTTCGACC TATCGTCGCC CCAGAAGAGC     720

GGTACGGGGC CGCAACCGGG TTCTGCCGGC ATGGGGGGCG CCAAAACGCC GTCGGACGCC     780

GTGCAGAACA TCCTCCAAAA GATCGAGAAG ATTAAGAACA CGGAGGAATA G              831

(2) INFORMATION FOR SEQ ID NO: 25:

(i) SEQUENCE CHARACTERISTICS:
        (A) LENGTH: 831 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 25:

TACCGATCGT ACTGACCACC TGTCGTTTAC CCAGCGGCCT AGGCGTACGC ACCGTCGGAG      60

AGAAGCGACC GGTTACGGCC GCCAGACGTA CTGCTGCCGG GCCCAGACCT ATTGCTAGAG     120

TACTTGCTCG GGTACCCAGA GCCGCCAGAC CCTCCTCCAC CGCCGCCACC GCCGTTCTTC     180

GTGCTGGCGC CACCGCCGCC ACCAAGGCCA TGCGCCTTTT ACTCATCGCC ACCGCCGCCG     240

CCACTAGTAC TGGTGCCAGA AAGGAGGTTC CTTTTTATGC TCGTCGTGTT CTAGTGGTCG     300

ATGGACTGCA GGTTTCCACC TAGCCCGCCG CCGCCTCCTC CTCCTCCGCC GCCAAACCTA     360

GCGTTGAGGC CGTTAATGAA GTTGCTGCGC TTTCTCCTCT CGCTGTCGCT CCTAAGACAT     420

TGCAAGCTCA AGCAGGGATT GTGGTTCTTC GTTTTCACGC CGTTCTAGGC GTACGTACCC     480

CAAGGCCCGC CGCCACGACC GCCCCCACCA CCTGCTCTGC ACTCGCCCCC GGGCTCGCTG     540

CCAGACCCAC CGCCAGCACC ACCACCCCCA CCACCCCTAA GGCCCCCTTA CTACCCCGCG     600

CCGCCAGCGT ACAACCCGCG ATCGCACCTG GCATGGATAG CCGAGTTAAG ATCTTTCTAG     660

GACTTCTCGT GCTGCCCGTA CTTTTGCCAC CGAAAGCTGG ATAGCAGCGG GGTCTTCTCG     720

CCATGCCCCG GCGTTGGCCC AAGACGGCCG TACCCCCCGC GGTTTTGCGG CAGCCTGCGG     780

CACGTCTTGT AGGAGGTTTT CTAGCTCTTC TAATTCTTGT GCCTCCTTAT C              831

(2) INFORMATION FOR SEQ ID NO: 26:

(i) SEQUENCE CHARACTERISTICS:
        (A) LENGTH: 276 amino acids
        (B) TYPE: amino acid
        (C) STRANDEDNESS: single
        (D) TOPOLOGY: linear
```

-continued (ii) MOLECULE TYPE: Polypeptide (v) FRAGMENT TYPE: internal (xi) SEQUENCE DESCRIPTION: SEQ ID NO: 26:

```
Met Ala Ser Met Thr Gly Gly Gln Gln Met Gly Arg Arg Ile Arg Met
1               5                   10                  15

Arg Gly Ser Leu Ser Ser Leu Ala Asn Ala Gly Gly Leu His Asp Asp
            20                  25                  30

Gly Pro Gly Leu Asp Asn Asp Leu Met Asn Glu Pro Met Gly Leu Gly
            35                  40                  45

Gly Leu Gly Gly Gly Gly Gly Gly Gly Lys Lys His Asp Arg Gly
    50                  55                  60

Gly Gly Gly Gly Ser Gly Thr Arg Lys Met Ser Ser Gly Gly Gly Gly
65                  70                  75                  80

Gly Asp His Asp His Gly Leu Ser Ser Lys Glu Lys Tyr Glu Gln His
                85                  90                  95

Lys Ile Thr Ser Tyr Leu Thr Ser Lys Gly Gly Ser Gly Gly Gly Gly
            100                 105                 110

Gly Gly Gly Gly Gly Gly Leu Asp Arg Asn Ser Gly Asn Tyr Phe Asn
            115                 120                 125

Asp Ala Lys Glu Glu Ser Asp Ser Glu Asp Ser Val Thr Phe Glu Phe
            130                 135                 140

Val Pro Asn Thr Lys Lys Gln Lys Cys Gly Lys Ile Arg Met His Gly
145                 150                 155                 160

Val Pro Gly Gly Gly Ala Gly Gly Gly Gly Arg Asp Val Ser Gly
            165                 170                 175

Gly Pro Ser Asp Gly Leu Gly Gly Arg Gly Gly Gly Gly Gly
            180                 185                 190

Asp Ser Gly Gly Met Met Gly Arg Gly Gly Arg Met Leu Gly Ala Ser
            195                 200                 205

Val Asp Arg Thr Tyr Arg Leu Asn Ser Arg Lys Ile Leu Lys Ser Thr
            210                 215                 220

Thr Gly Met Lys Thr Val Ala Phe Asp Leu Ser Ser Pro Gln Lys Ser
225                 230                 235                 240

Gly Thr Gly Pro Gln Pro Gly Ser Ala Gly Met Gly Gly Ala Lys Thr
            245                 250                 255

Pro Ser Asp Ala Val Gln Asn Ile Leu Gln Lys Ile Glu Lys Ile Lys
            260                 265                 270

Asn Thr Glu Glu
        275
```

We claim:

1. An isolated polypeptide consisting of the amino acid sequence set forth in SEQ ID NO: 1 or fragments thereof, wherein said fragments bind to IgM antibodies raised against human cytomegalovirus.

2. The isolated polypeptide of claim 1 wherein said fragment consists of at least 25 amino acids.

3. The isolated polypeptide of claim 1 wherein said fragment consists of at least 10 amino acids.

4. A fusion protein comprising:
   (a) the isolated polypeptide of claim 1, and
   (b) a second polypeptide that is not cytomegalovirus protein UL/57.

5. The fusion protein of claim 4 wherein the second polypeptide is a human cytomegalovirus polypeptide other than UL/57.

6. The fusion protein of claim 5 wherein said cytomegalovirus polypeptide is selected from the group consisting of a polypeptide derived from p52, a polypeptide derived from pp65, a polypeptide derived from pp71, a polypeptide derived from pp28, a polypeptide derived from gp 116/58, and a polypeptide derived from tegument protein pp150.

7. The fusion protein of claim 6 wherein the second polypeptide is cytomegalovirus tegument protein pp 150 C terminal region.

8. The fusion protein of claim 4 wherein the second polypeptide is not a human cytomegalovirus protein.

9. The fusion protein of claim 8 wherein said second polypeptide is glutathione S transferase.

10. The fusion protein of claim 9 wherein the second polypeptide is no more than 25 amino acids.

11. The fusion protein of claim 4 wherein said second polypeptide consists of at least 25 amino acids.

12. The fusion protein of claim 4 wherein said second polypeptide consists of at least 10 amino acids.

13. The fusion protein of claim 6 wherein said second polypeptide is the C terminal region of pp 52.

14. The fusion protein of claim 5 wherein said cytomegalovirus polypeptide consists of an amino acid sequence selected from the group consisting of SEQ ID NO: 23 and SEQ ID NO: 26.

15. The fusion protein of claim 5 wherein said cytomegalovirus polypeptide consists of an amino acid sequence selected from the group consisting of amino acids 18–154 of SEQ ID NO: 23 and amino acids 222–276 of SEQ ID NO: 26.

16. The fusion protein of claim 4 further comprising a third polypeptide that is not cytomegalovirus protein UL57.

17. The fusion protein of claim 16 wherein said third polypeptide is derived from a human cytomegalovirus protein.

18. The fusion protein of claim 17 wherein said second polypeptide is human cytomegalovirus tegument protein pp150 C terminal and wherein said third polypeptide is derived from pp52.

19. The fusion protein of claim 16 further comprising a polypeptide which is derived from glutathione S transferase.

20. A composition comprising the isolated polypeptide of claim 1 bound to a solid phase.

21. A composition comprising the fusion protein of claim 4 bound to a solid phase.

22. A composition comprising the fusion protein of claim 16 bound to a solid phase.

23. A test kit, comprising:

a container;

a support surface; and an antigen bound to said support surface, wherein said antigen is the isolated polypeptide of claim 1 or the fusion protein of claim 4 or both, wherein said support surface and bound antigen are packaged within said container.

24. The test kit of claim 23 further comprising an antibody which specifically binds to said antigen and wherein said antibody is labeled with an enzyme.

25. A method for determining presence of antibodies against human cytomegalovirus, comprising contacting a sample to be investigated with the isolated polypeptide of claim 1 or the fusion protein of claim 4 and determining binding of antibodies thereto as a determination of antibodies against human cytomegalovirus in said sample.

26. The method of claim 25 further comprising contacting said sample with an antibody which specifically binds to said isolated polypeptide, wherein said antibody is coupled with an indicator molecule.

27. The method of claim 26 wherein said indicator molecule is horseradish peroxidase.

\* \* \* \* \*